United States Patent [19]

Vander Jagt et al.

[11] Patent Number: 6,124,498
[45] Date of Patent: Sep. 26, 2000

[54] HYDROXYNAPHTHOIC ACIDS AND DERIVATIVES

[75] Inventors: David L. Vander Jagt; Lorraine M. Deck, both of Albuquerque; Robert E. Royer, Bosque Farms, all of N. Mex.

[73] Assignee: University Of New Mexico, Albuquerque, N. Mex.

[21] Appl. No.: 09/066,675

[22] Filed: Apr. 28, 1998

Related U.S. Application Data

[63] Continuation-in-part of application No. 08/988,472, Dec. 10, 1997, which is a continuation of application No. 08/431,294, Apr. 28, 1995.
[60] Provisional application No. 60/045,083, Apr. 29, 1997.
[51] Int. Cl.$^7$ .......................... C07C 63/34; C07C 69/76; C07C 233/00
[52] U.S. Cl. ........................... 562/467; 560/56; 562/840; 562/867; 564/172
[58] Field of Search ................................ 562/467, 840, 562/867; 564/172; 560/56

[56] References Cited

U.S. PATENT DOCUMENTS 4,137,272  1/1979  Papenfuhs et al. .

FOREIGN PATENT DOCUMENTS 647997  12/1950  United Kingdom .

OTHER PUBLICATIONS

Bryant, C., et al., "The Incorporation of Radioactivity from [$^{14}$C] Glucose into the Soluble Metabolic Intermediates of Malaria Parasites," (1964), *Am J Trop Med Hyg 13*, 515–519.

Scheibel, L.W. et al., "Carbohydrate Metabolism in *Plasmodium knowlesi*," (1970), *Comp Biochem Physiol 37*, 543–553.

Shakespeare, P.G. et al., "Glucose Catabolism by the Simian Malaria Parasite *Plasmodium knowlesi*," (1973), *Nature 241*, 538–540.

Vander Jagt, D.L., et al., "D–Lactate Production in erthrocytes infected with *Plasmodium falciparum*,"(1990), *Mol Biochem Parasitology 42*, 277–284.

Sherman, I.W., "Biochemistry of Plasmodium (Malarial Parasites)," (1979), *Microbiological Reviews 43*, 453–495.

Certa, U., et al., "Aldolase Activity of a *Plasmodium falciparum* Protein with Protective Properties," (1988), *Science 240*, 1036–1038.

Kaslow, D.C. et al., "Cloning Metabolic Pathway Genes by Complementation in *Escherichia coli*," (1990), *Journal of Biological Chemistry 265*, 12337–12341.

Hicks, K.E., et al., "Glycolytic Pathway of the Human Malaria Parasite *Plasmodium falciparum*: primary sequence analysis of the gene encoding 3–phosphate kinase and chromosomal studies," (1991), *Gene 100*, 123–129.

Bzik et al. "Expression of *Plasmodium falciparum* Lactate Dehydrogenase in *Escherichia coli*," (1993), *Molecular and Biochemical Parasitology 59*, 155–166.

Read, M., et al., "Molecular Characterisation of the Enolase Gene from the Human Malaria Parasite *Plasmodium falciparum*," (1994), *Eur. J. Biochem 220*, 513–520.

Olafsson, P., et al., "Molecular Analysis of *Plasmodium falciparum* Hexokinase," (1992), *Molecular and Biochemical Parasitology 56*, 89–102.

Ranie, J., et al., "Cloning of the Triosephosphate Isomerase Gene of *Plasmodium falciparum* and Expression in *Escherichia coli*,"(1993), *Mol. Biochem. Parasitology 61*, 159–169.

Vander Jagt, D.L., et al., "Partial Purification and Characterization of Lactate Dehydrogenase from *Plasmodium falciparum*," (1981), *Molecular and Biochemical Parasitology 4*, 255–264.

Eventhoff, W., et al., "Structural Adaptations of Lactate Dehydrogenase Isozymes," (1977), *Proc Natl Acad Sci USA 74*, 2677–2681.

Grau, U.M., et al., "Structure of the Active Ternary Complex of Pig Heart Lactate Dehydrogenase with S–lac–NAD at 2•7 Å Resolution," (1981), *J Mol Biol 151*, 289–307.

Dunn, C.R., et al., "Design and Synthesis of New Enzymes Based on the Lactate Dehydrogenase Framework," (1991), *Phil Trans R Soc Lond B 332*, 177–184.

(List continued on next page.)

*Primary Examiner*—Paul J. Killos
*Attorney, Agent, or Firm*—Jagtiani & Associates

[57] ABSTRACT

In one embodiment, the present invention provides a compound comprising:

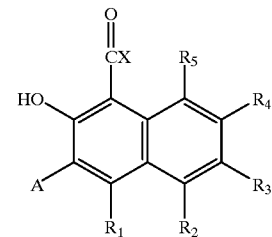

wherein

A=H or OH

X=OH, a halogen, OR, NHR, NR'R" where R, R', and R"=H, $C_{1-8}$ alkyl, $C_{2-8}$ alkenyl, or $C_{2-8}$ alkynyl, cycloalkyl, cycloalkenyl, aryl, aralkyl or heterocyclic, substituted or unsubstituted; and $R_1$, $R_2$, $R_3$, $R_4$, $R_5$=H, $C_{1-8}$ alkyl, $C_{2-8}$ alkenyl, or $C_{2-8}$ alkynyl, cycloalkyl, cyloalkenyl, aryl or heterocyclic, substituted or unsubstituted, wherein $R_1$ includes at least one methylene spacer through which $R_1$ is attached to said compound. The present invention also provides methods for making hydroxynaphthoic acids.

26 Claims, 14 Drawing Sheets

OTHER PUBLICATIONS

Dunn, C.R., et al., "The Structure of Lactate Dehydrogenase from *Plasmodium falciparum* Reveals a New Target for Anti–Malarial Design," (1996), *Nature Structural Biology 3*, 912–915.

Makler, M.T. et al., "Measurement of the Lactate Dehydrogenase Activity of *Plasmodium falciparum* as an Assessment of Parasitemia," (1993), *Am J Trop Med Hyg 48*, 205–210.

Makler, M.T., et al., "Parasite Lactate Dehydrogenase as an Assay for *Plasmodium falciparum* Drug Sensitivity," (1993), *Am J Trop Med Hyg 48*, 739–741.

Royer, R.E., et al., "Biologically Active Derivatives of Gossypol: Synthesis and Antimalarial Activities of Peri–Acylated Gossylic Nitriles," (1986), *Journal of Medicinal Chemistry 29*, 1799–1801.

Wilks, H.M., et al., "Design of a Specific Phenyllactate Dehydrogenase by Peptide Loop Exchange on the *Bacillus stearothermophilus* Lactate Dehydrobenase Framework," (1992), *Biochemistry 31*, 7802–7806.

Deck, L.M., et al., "Gossypol and Derivatives: A New Class of Aldose Reductase Inhibitors," (1991), *Journal of Medicinal Chemistry 34*, 3301–3305.

Royer, R.E., et al., "Synthesis and Anti–HIV Activity of 1,1 –Dideoxygossypol and Related Compounds," (1995), *Journal of Medicinal Chemistry 38*, 2427–2432.

Geren, L.M. et al., "*Fluorescence Energy Transfer Studies of the Interaction Between Adrenodoxin and Cytochrome c*," (1981), *J Biol Chem 256*, 10485–10489.

Royer, R.E., et al., "Binding of Gossypol Derivatives to Human Serum Albumin," (1988), *Journal of Pharmaceutical Sciences 77*, 237–240.

Westheimer, F.H., 1987, in Coenzymes and cofactors, vol. IIA–pyridine nucleotide coenzymes, ed. D. Dolphin, O. Avramovic and R. Poulson, pp. 253–322, John Wiley, New York.

Wilks, H.M., et al., "A Specific, Highly Active Malate Dehydrogenase by Redesign of a Lactate Dehydrogenase Framework," (1988), *Science 242*, 1541–1544.

Samama, J–P., et al., "An Investigation of the Active Site of lactate Dehydrogenase with $NAD^+$ Analogues," (1981), *Eur. J. Biochem. 120*, 563–569.

Sakai, I., et al., "The cDNA and Protein Sequences of Human Lactate Dehydrogenase B," (1987), *Biochem. J. 248*, 933–936.

Tsujibo, H., et al., "Nucleotide Sequences of the cDNA and an Intronless Pseudogene for Human Lactate Dehydrogenase–A Isozyme," (1985), *Eur. J. Biochem. 147*, 9–15.

Stangl, D., et al., "Structure and Function of L–Lactate Dehydrogenases from Thermophilic and Mesophilic Bacteria, V," (1987), *Biol. Chem. Hoppe–Seyler 368*, 1157–1166.

Kunai, K. et al., "Nucleotide Sequence and Characteristics of the Gene for L–Lactate Dehydrogenase of *Thermus caldophilus* GK24 and the Deduced Amino–Acid Sequence of the Enzyme," (1986), *Eur. J. Biochem. 160*, 433–440.

Verlinde, C.L.M.J., et al., "Selective Inhibition of Trypanosomal Glyceraldehyde–3–phosphate Dehydrogenase by Protein Structure–Based Design: Toward New Drugs for the Treatment of Sleeping Sickness," (1994), *Journal of Medicinal Chemistry 37*, 3605–3613.

Gomez, M. A., et al., "Substrate and Cofactor Specificity and Selective Inhibition of Lactate Dehydrogenase from the Malarial Parasite *P. falciparum*, " (1997), *Molecular and Biochemical Parasitology 90*, 235–246.

Ranie, Jamuna, et al., Cloning of the triosephosphate isomerase gene of *Plasmodium falciparum* and expression in *Escherichia coli* from *Molecular and Biochemical Parasitology*, 61 (1993) 159–170.

Geren, Lois M. and Francis Millett, Fluorescence Energy Transfer Studies of the Interaction between Adrenodoxin and Cytochrome c* from *The Journal of Biological Chemistry*, vol. 256, No. 20, Issue of Oct. 25, pp. 10485–10489, 1981.

Sherman, Irwin W., Biochemistry of Plasmodium (Malarial Parasites) from *Microbiological Reviews*, Dec. 1979, p. 453–495.

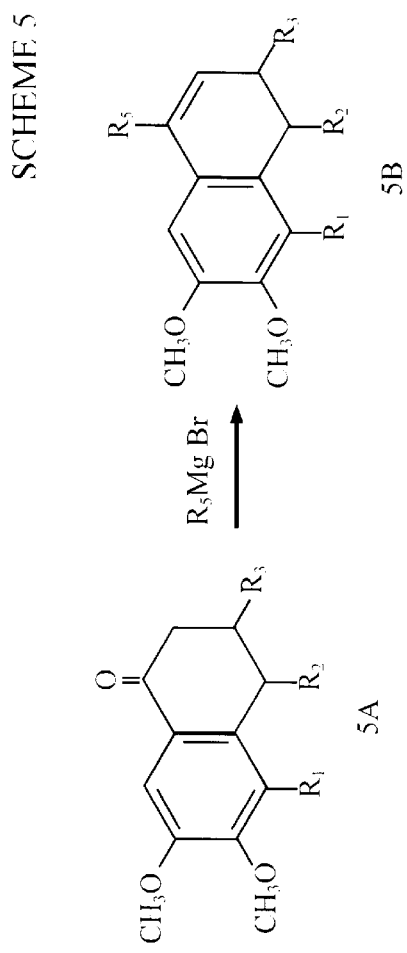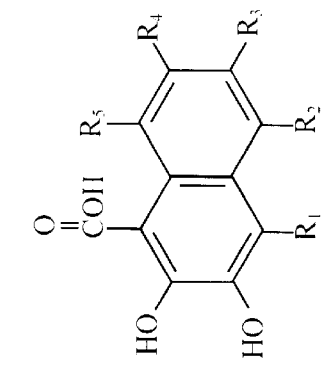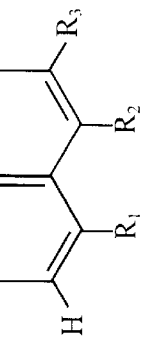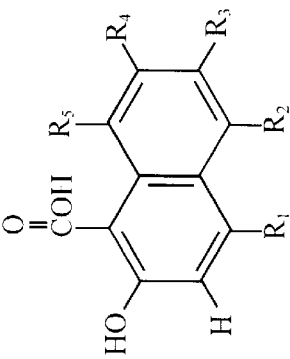
SCHEME 5
FIG. 5
SCHEME 6
FIG. 6

SCHEME 9

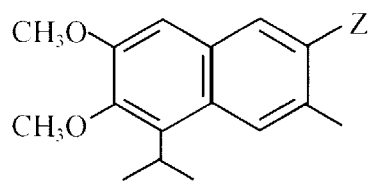

22a: Z = Br
23a: Z = CH$_3$
23b: Z = CH$_2$C$_6$H$_5$
23c: Z = CH$_2$C$_6$H$_4$CF$_{3\ (para)}$
23d: Z = CH$_2$C$_6$H$_4$CH$_{3(para)}$
23e: Z = CH$_2$C$_6$H$_4$CH$_{3(ortho)}$
23f: Z = CH$_2$C$_6$H$_4$CH$_{3(meta)}$
23g: Z = CH$_2$C$_6$H$_4$Cl$_{(para)}$

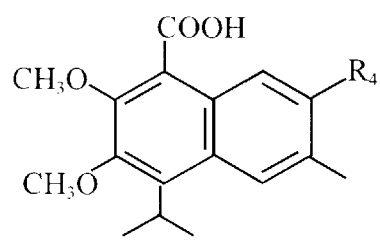

24a: R$_4$ = CH$_3$
24b: R$_4$ = CH$_2$C$_6$H$_5$
24c: R$_4$ = CH$_2$C$_6$H$_4$CF$_{3\ (para)}$
24d: R$_4$ = CH$_2$C$_6$H$_4$CH$_{3(para)}$
24e: R$_4$ = CH$_2$C$_6$H$_4$CH$_{3(ortho)}$
24f: R$_4$ = CH$_2$C$_6$H$_4$CH$_{3(meta)}$
24g: R$_4$ = CH$_2$C$_6$H$_4$Cl$_{(para)}$

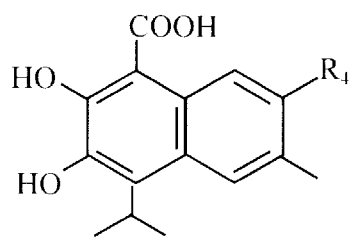

25a: R$_4$ = CH$_3$
25b: R$_4$ = CH$_2$C$_6$H$_5$
25c: R$_4$ = CH$_2$C$_6$H$_4$CF$_{3\ (para)}$
25d: R$_4$ = CH$_2$C$_6$H$_4$CH$_{3(para)}$
25e: R$_4$ = CH$_2$C$_6$H$_4$CH$_{3(ortho)}$
25f: R$_4$ = CH$_2$C$_6$H$_4$CH$_{3(meta)}$
25g: R$_4$ = CH$_2$C$_6$H$_4$Cl$_{(para)}$

FIG. 9

Table 1

| Inhibition of Human Lactate Dehydrogenase (LDH-H$_4$ and LDH-M$_4$) and Malarial Parasite *P. faciparum* Lactate Dehydrogenase (pLDH) by Dihydroxynapthoic Acids. | | | |
|---|---|---|---|
| Inhibitor | LDH-M$_4$ | KI (µM) LDH-H$_4$ | pLDH |
| 21a | 34 | >250 | 22 |
| 21b | 4 | 190 | 13 |
| 21c | 0.5 | 39 | 8 |
| 13 | 3 | 91 | 2 |
| 25a | 2 | 78 | 1 |
| 25b | 0.2 | 7 | 0.7 |
| 25c | 13 | 81 | 0.2 |
| 25d | 0.03 | 8 | 0.1 |
| 21d | 1 | 49 | 6 |
| 21e | 0.1 | 19 | 0.1 |
| 21f | 0.05 | 1 | 0.3 |

All data at pH 7.5, 25°C.

FIG. 10

HYDROXYNAPHTHOIC ACIDS AND DERIVATIVES

RELATED APPLICATION

The present application is based on U.S. Provisional Patent Application No. 60/045,083 filed Apr. 29, 1997, the entire disclosure and contents of which is hereby incorporated by reference. The present application is also a continuation-in-part of U.S. patent application Ser. No. 08/988,472 filed Dec. 10, 1997 which itself is a continuation application of U.S. patent application Ser. No. 08/431,294 filed Apr. 28, 1995. The entire disclosures and contents of both these applications are hereby incorporated by reference.

BACKGROUND OF THE INVENTION

1. Field of the Invention

The present invention relates to naphthoic acids and derivatives.

2. Description of the Prior Art

Structure-based drug design is a rapidly expanding field that combines synthetic chemistry, enzymology, modeling and crystallography in the targeted development of new drugs. An essential element of structure-based drug design is identification of a lead compound, whether from random screening or from computational procedures, that can be developed into an improved inhibitor through the iterative process of 1) determination of the three-dimensional structure of the complex of the target receptor and lead compound, 2) optimization of inhibitor-receptor interactions through molecular modeling; 3) synthesis of a new inhibitor; and 4) testing of the new inhibitor.

Most drugs are targeted at the active sites of enzymes and other proteins. There are numerous dehydrogenases with critical metabolic roles that represent potential drug targets. The NAD(H) or NADP(H) cofactor binding sites of dehydrogenases have not been widely developed as drug targets, mainly because the structures of cofactor binding sites of dehydrogenases, as determined by x-ray crystallography, are often quite similar, which implies that development of selective dehydrogenase inhibitors will be difficult. There has been some success in developing selective inhibitors that compete for the adenosine part of the cofactor binding site. For example, structure based design of adenosine-related inhibitors of glyceraldehyde-3-P dehydrogenase from trypanosomes has been reported. There has also been some success in developing NAD analogs as potential therapeutics. For example, the anticancer agent tiazofurin (2-β-D-ribofuranosylthiazole-4 carboxamide) is metabolically converted into the NAD analog thiazole-4-carboxamide adenine dinucleotide which is a potent inhibitor of IMP dehydrogenase type 11, the dominant isoenzyme in neoplastic cells. Generally, however, the nicotinamide part of the dinucleotide binding site of dehydrogenases has not been a target in drug design.

SUMMARY OF THE INVENTION

It is therefore an object of the present invention to provide Pan-Active Site inhibitors of dehydrogenases.

In one embodiment, the present invention provides a compound comprising:

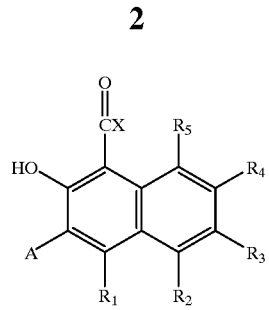

wherein:
A=H or OH
X=OH, a halogen, OR, NHR, NR'R" where R, R', and R"=H, $C_{1-8}$alkyl, $C_{2-8}$ alkenyl, or $C_{2-8}$ alkynyl, cycloalkyl, cycloalkenyl, aryl, aralkyl or heterocyclic, substituted or unsubstituted; and
$R_1$, $R_2$, $R_3$, $R_4$, $R_5$=H, $C_{1-8}$ alkyl, $C_{2-8}$ alkenyl, or $C_{2-8}$ alkynyl, cycloal cyloalkenyl, aryl or heterocyclic, substituted or unsubstituted, wherein $R_1$ includes at least one methylene spacer through which $R_1$ is attached to said compound.

In another embodiment, the present invention also provides methods for making hydroxynaphthoic acids.

Other objects and features of the present invention will be apparent from the following detailed description of the preferred embodiments.

BRIEF DESCRIPTION OF THE DRAWINGS

The invention will be described in conjunction with the accompanying drawings, in which:

FIG. 5 illustrates a method for incorporating specific $R_5$ radical groups into the naphthoic acids of the present invention at the 8-position;

FIG. 6 illustrates how monohydroxy bromides useful in the methods of the present invention can be synthesized from a readily available aldehyde starting materials;

FIG. 9 illustrates methods for making compounds of the present invention;

FIG. 10 is a table showing inhibition of human lactate dehydrogenase (LDH-$H_4$ and LDH-$M_4$) and malarial parasite *P. faciparum* lactate dehydrogenase (pLDH) by dihydroxynaphthoic acids;

DETAILED DESCRIPTION OF THE PREFERRED EMBODIMENTS

Definitions

Figure 1:
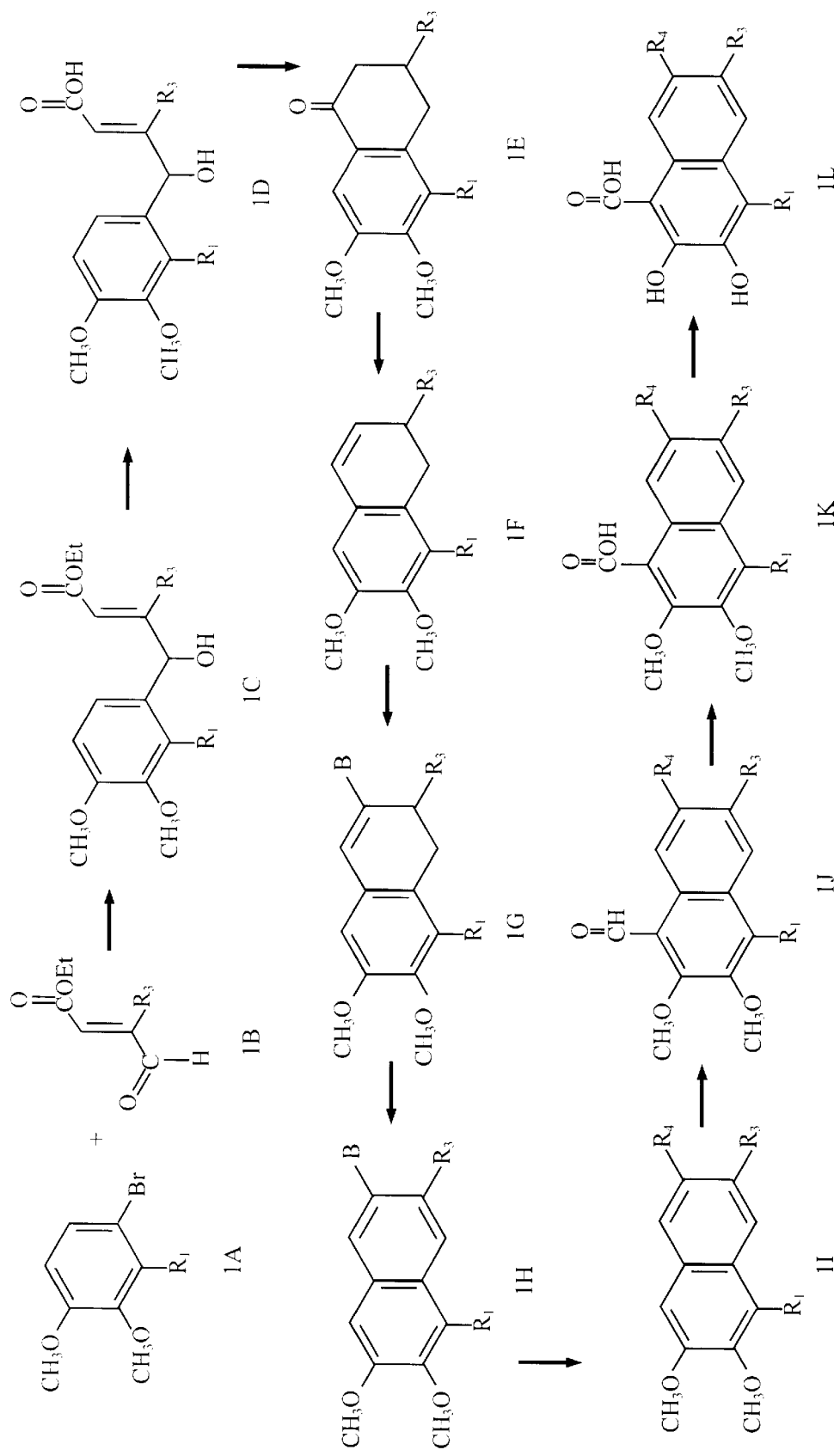
FIG. 1 illustrates a method for making dihydroxynaphthoic acids of the present invention having a particular radical group at the 7-position.

For the purposes of the present specification and claims, the following terms, unless specifically indicated otherwise, have the following meanings:

The term "substituent" refers to a radical group which replaces a hydrogen on another radical group or on a compound.

The term "substituted" refers to a radical group including an alkyl, alkenyl, or alkynyl substituent or a functional group substituent such as halide, e.g. fluoride, chloride, bromide or iodide; carboxylate; nitro, etc. For the purposes of the present specification and claims, where the terms "substituted" or "unsubstituted" follow a list of radical groups, these terms refer to all of the preceding radical groups in the list.

The term "halogen" refers to any of F, Cl, Br, or I.

The term "methylene spacer" refers to a —$CH_2$—, —$CHX_1$—, or —$CX_1X_2$— group where each of $X_1$ and $X_2$ is a substituent or a radical group.

The term "$C_{1-8}$ alkyl" refers to a straight or branched chain alkyl radical group having one to eight carbon atoms including for example, methyl, ethyl, propyl, isopropyl, butyl, sec-butyl, isobutyl, pentyl, dimethyl-propyl, hexyl, t-octyl and octyl, and cognate terms (such as "$C_{1-8}$ alkoxy") are to be construed accordingly. Similarly, the term "$C_{1-5}$ alkyl" refers to a straight or branched chain alkyl radical group having one to five carbon atoms (such as methyl or ethyl).

The term "$C_{2-8}$ alkenyl" refers to a straight or branched chain alkyl radical group having one to eight carbon atoms and having in addition at least one double bond of either E or Z stereochemistry where applicable. This term would include, for example, vinyl, 1-propenyl, 1- and 2-butenyl and 2-methyl-2-propenyl.

The term "$C_{2-8}$ alkynyl" refers to a straight or branched chain alkyl radical group having one to eight carbon atoms and having in addition at least one triple bond. This term would include, for example, propargyl, 1- and 2-butynyl, etc.

The term "$C_{3-8}$ cycloalkyl" refers to a saturated cyclic radical group having from 3 to 8 carbon atoms arranged in a ring and includes, for example, cyclopropyl, cyclobutyl, cyclopentyl, cyclohexyl, cyclooctyl, etc.

The term "$C_{3-8}$ cycloalkenyl" refers to an unsaturated cyclic radical group having from 3 to 8 carbon atoms arranged in a ring and includes, for example, cyclohexenyl, cyclohexadienyl, etc..

The term "aryl" refers to a radical group having the ring structure characteristic of benzene, naphthalene, phenanthrene, anthracene, pyrene, benzopyrene, etc.

The term "aralkyl" refers to a substituted aryl radical group having one or more $C_{1-8}$ alkyl substituents regardless of whether the link to a compound or radical group is through the alkyl or the aryl of the aralkyl radical group.

The term "heterocyclic" refers to a radical group having one or more ring structures in which one or more atoms in the ring structure is an element other than carbon such as sulfur, nitrogen, oxygen, etc.

For the purposes of the present invention, including the accompanying drawing figures, the possible values for the radicals $R_1$, $R_2$, $R_3$, $R_4$, and $R_5$ are set forth above in the summary of the invention section.

Description

Various methods can be used to synthesize the compounds of the present invention:

For example, Scheme 1 in FIG. 1 shows how to synthesize dihydroxynaphthoic acids of the invention having a particular radical group $R_4$ at the 7-position (1L). A known 1-bromo-3,4-dimethoxy-benzene (1A), such as bromo-3,4-dimethoxy-2-isopropylbenzene, is reacted with a known ethyl 4-oxobut-2-enoate (1B), such as ethyl 3-methyl-4-oxobut-2-enoate, to form an ester (1C). Because the ester, 1C, is difficult to reduce it is saponified to the acid (1D), which is hydrogenolyzed and reduced. The resulting carboxylic acid is cyclized with polyphosphoric ester to give tetralone (1E). The ketone function of 1E is reduced with sodium borohydride and the intermediate alcohol dehydrated on acidic workup to form an alkene (1F). Addition of bromine to the 1F forms a dibromide which is immediately dehydrohalogenated with dimethylformamide to form vinyl bromide (1G) which is dehydrogenated with 2,3-dichloro-5,6-dicyano-1,4-benzoquinone to form a bromonaphthalene (1H). Compound 1H is reacted with n-butyl lithium and benzaldehyde to form a benzylic alcohol which is hydrogenolyzed with palladium on charcoal in ethanol to form 1I where $R_4$ is benzyl. Formation of the compound 1I where $R_4$ is methyl is accomplished by reaction of 1H with n-butyl lithium and methyl iodide. Carbonyl groups are introduced to the compound 1I by formylation with titanium tetrachloride and dichloromethyl methyl ether to form 1J. Oxidation of the aldehydes with sodium hypochlorite form a carboxylic acids 1K. The methyl groups are removed from the phenolic ether 1K with boron tribromide to form compound 1L.

Figure 2:
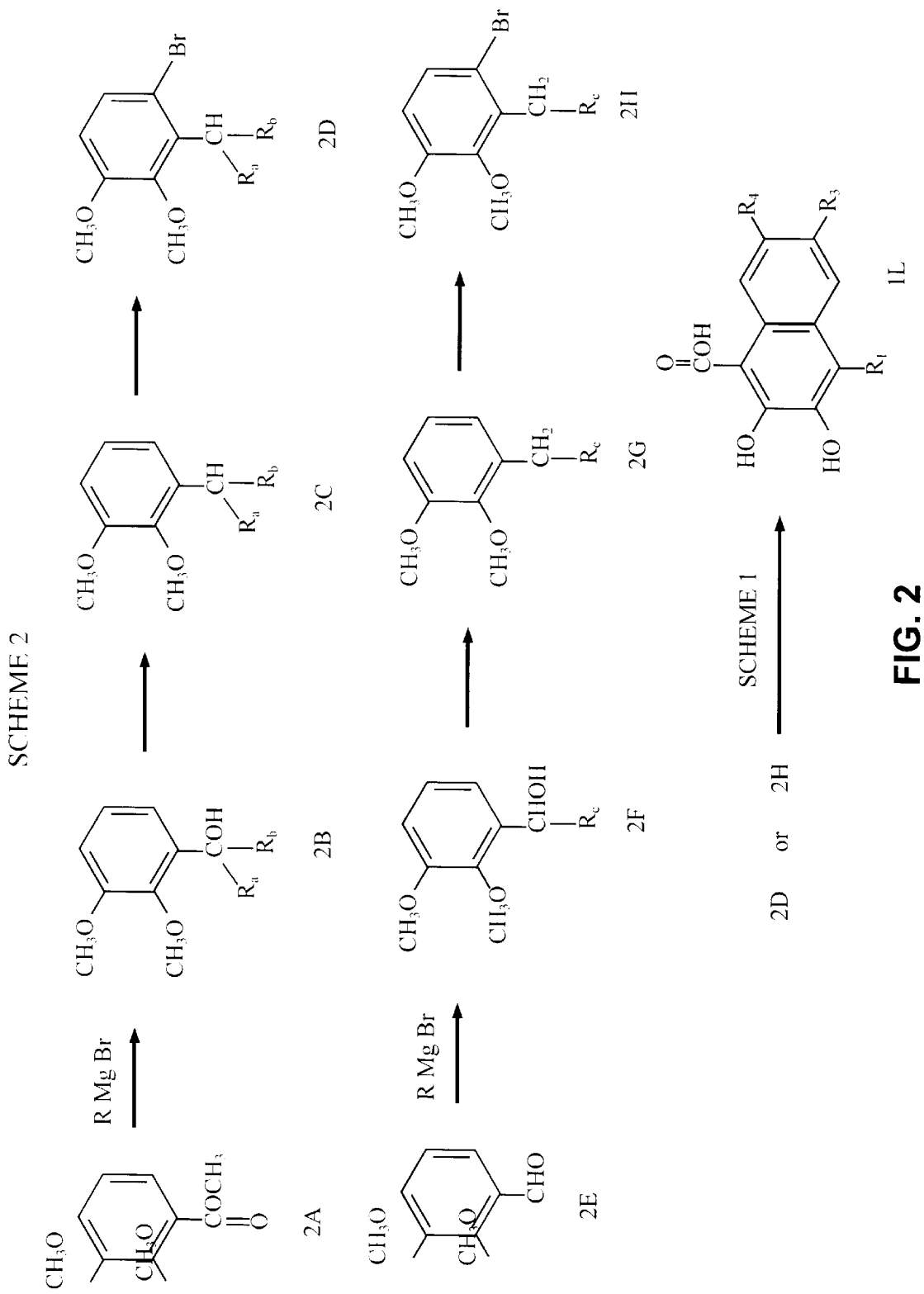
FIG. 2 illustrates methods of making of bromides which can be used as the starting bromide in the method illustrated in FIG. 1.

Scheme 2 in FIG. 2 illustrates efficient syntheses of bromides (2D) and (2H) which can be used as the starting bromide (1A) of scheme 1 having a specific radical group $R_1$ (In Scheme 2, radical groups $R_a$, $R_b$, and $R_c$ can be almost any radical group, just as groups $R_1$, $R_2$, $R_3$, $R_4$, and $R_5$ can be almost any radical group). Compound 2A is synthesized from 3-methoxysalicylic acid by methylation using dimethylsulfate and potassium carbonate in acetone. Grignard reaction of 2A with a Grignard reagent, such as methylmagnesium bromide, affords alcohol (2B). Hydrogenolysis of 2B with 10% palladium on charcoal in ethyl acetate afforded compound (2C). Bromination using bromine in carbon tetrachloride at −10C. afforded compound (2D). Compound (2H) can be synthesized by the same methodology except that 2,3-dimethoxybenzaldehyde is the starting material. In scheme 2, the synthesis of (2D) represents a pathway for introducing two radical groups ($R_a$ and $R_b$), while the synthesis of (2H) represents the introduction one radical group ($R_c$) attached to bromide by a methylene spacer. Furthermore, by varying the radical group $R_4$ of the starting bromide (1A), the method of scheme 1 can be used to synthesize families of dihydroxynaphthoic acids having different radical groups $R_4$.

Figure 3:
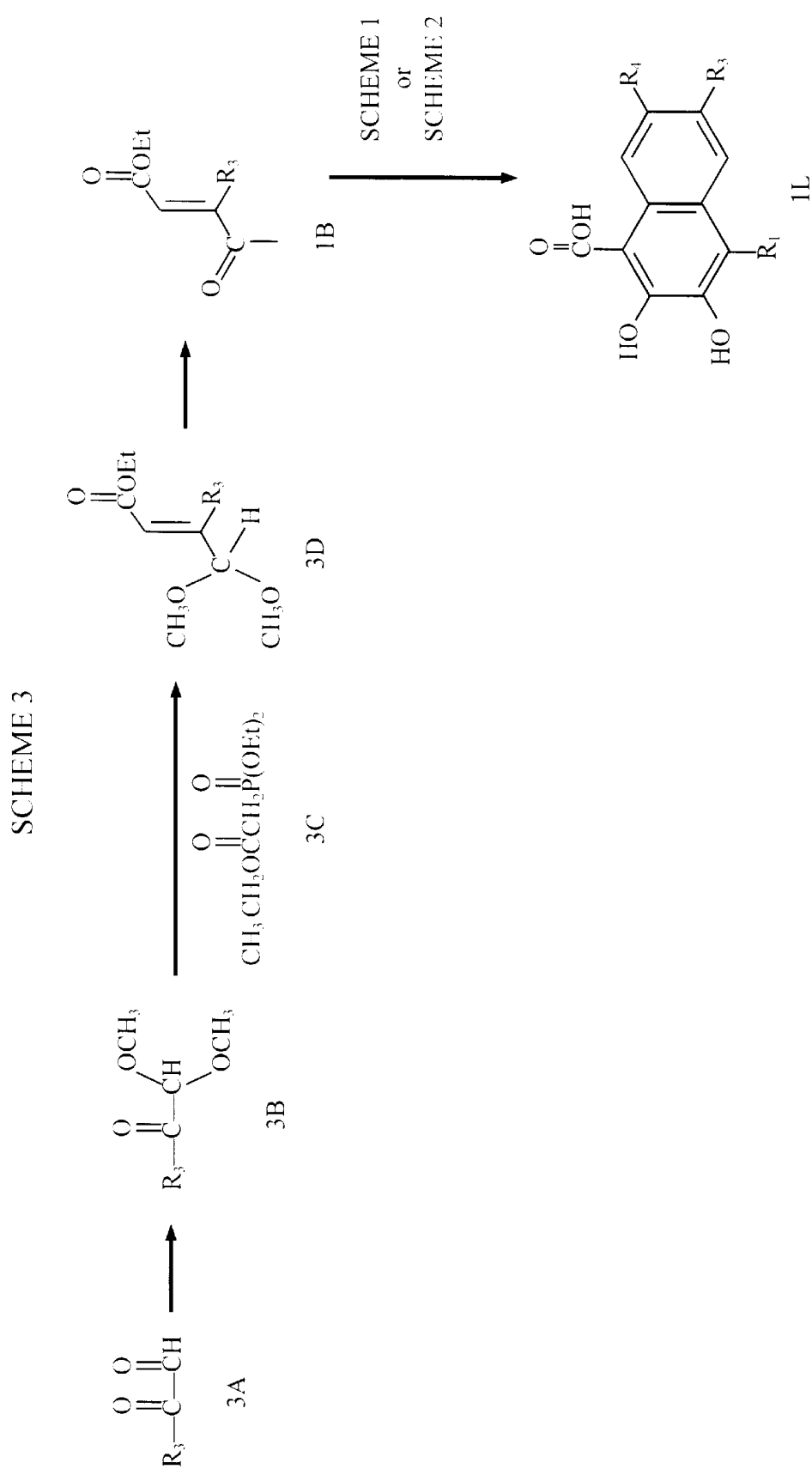
FIG. 3 illustrates a method for incorporating specific $R_3$ radical groups into the naphthoic acids of the present invention.

Scheme 3 in FIG. 3 illustrates a method for incorporating specific $R_3$ radical groups into the naphthoic acids of the present invention. A substituted glyoxal (3A) is converted to an acetals (3B) by reaction with methanol in the presence of acid. Reaction of 3B with triethylphosphonoacetate (3C) using a modification of the Wadsworth Emmons reaction affords compound 3D. Hydrolysis in dilute acid affords the aldehyde (1B). Compounds 1B can be used to form naphthoic acids as described in scheme 1.

Figure 4:
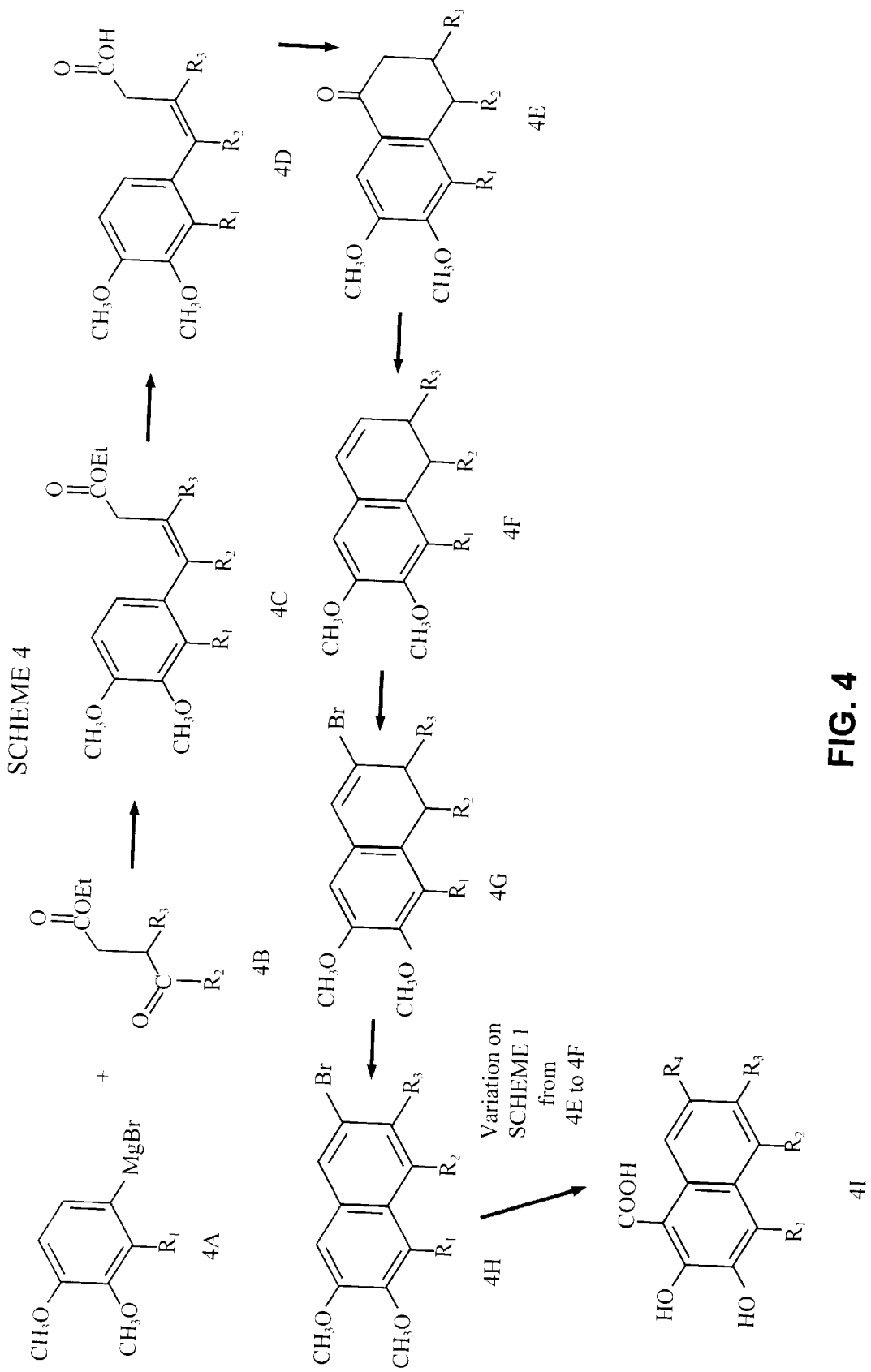
FIG. 4 illustrates a method for incorporating specific $R_2$ radical groups into the naphthoic acids of the present invention at the 5-position.

Scheme 4 in FIG. 4 illustrates a method for incorporating specific $R_2$ radical groups into the naphthoic acids of the present invention at the 5-position. Grignard reagent (4A), which can be derived from 1A, is reacted with a γ-keto ester (4B) under kinetic conditions and reaction takes place at the more reactive ketone site to form an alcohol which is then dehydrated to form resulting β, γ unsaturated ester (4C). 4B is a substituted γ-keto-ethyl ester which is readily available or which can be prepared easily using well known methods. Because the ester (4C) is difficult to reduce it is saponified to the acid (4D), which is hydrogenolyzed and reduced. The resulting carboxylic acid is cyclized with polyphosphoric ester to give tetralone (4E). The ketone function of 4E is reduced with sodium borohydride and the intermediate alcohol dehydrated on acidic workup to form an alkene (4F). Addition of bromine to the 4F forms a dibromide which is immediately dehydrohalogenated with dimethylformamide to form vinyl bromide (4G) which is dehydrogenated with 2,3-dichloro-5,6-dicyano-1,4-benzoquinone to form a bromonaphthalene (4H, which is equivalent to 1H in scheme 1). Compound of the present invention (41) can then be formed by following the steps from 1H to 1L in scheme 1.

Scheme 5 in FIG. 5 illustrates a method for incorporating specific $R_5$ radical groups into the naphthoic acids of the present invention at the 8-position. A tetralone like compound 5A whose preparation is described in scheme 1 is reacted with a Grignard reagent to form an alcohol which will dehydrate upon workup to afford an alkene having the structure of intermediate compound 5B. Intermediate compound (5B) can then be used to synthesize a naphthoic acid of the present invention (5C) by substituting intermediate compound (5B) for intermediate compound (1I) in scheme 1.

Although schemes 1 through 5 only specifically illustrate how to synthesize dihydroxynaphthoic acids of the present invention, the present invention also provides monohydroxynaphthoic acids as well. Scheme 6 in FIG. 6 illustrates how monohydroxy bromide (6B) can be synthesized from a readily available aldehyde starting material (6A). Benzaldehyde (6A) is reacted with a Grignard reagent, dehydrated, hydrogenolyzed, and then brominated to form bromide (6B). Bromide (6B) can then be substituted for (1A) in schemes 1 through 5 to produce monohydroxynaphthoic acids of the present invention having any of the radical groups $R_1$, $R_2$, $R_3$, $R_4$, and $R_5$ at the appropriate positions on the naphthoicalene ring.

Although the methods illustrated in schemes 1 through 6 only specifically show how to synthesize naphthoic acids of the present invention, it should be clear that corresponding naphthoic acid derivatives of the present invention can be readily formed by derivatizing the carboxylic acid group of the naphthoic acids by well known methods. For example, ethyl and methyl ester derivatives can be formed using the Fischer esterification process on the naphthoic acids of the present invention. Similarly, amide derivatives of the present invention can be formed by reacting the naphthoic acids of the present invention with dicyclohexylcarbodiimide (DCC) in the solvent methylene chloride. As is well known, any suitable amine can be used in this procedure.

In addition to providing hydroxynaphthoic acids and derivatives in a purified form, the present invention also provides hydroxynaphthoic acids and derivatives as present in a combinatorial library. In its broadest form, a combinatorial library can be defined as any ensemble of molecules. Most progress has been made in developing and, especially, in screening very large peptides or oligonucleotide libraries for ligands with high selectivity for a designated target. Numerous methodologies have been developed to prepare and to screen these libraries. In principle, many of these technologies are applicable to the development of libraries of small organic chemicals. However, screening of very complex mixtures of organic molecules is difficult compared to screening peptides or oligonucleotide libraries. Peptide libraries, such as phage display libraries, combine the power of genetics to screen libraries while oligonucleotide libraries utilize PCR (polymerase chain reaction) to amplify candidate ligands. One widely used strategy to develop chemical libraries is the split-synthesis method, where a starting material is divided into aliquots that are treated separately with different reagents, pooled, then split into the desired number of samples for the next reaction cycle. This split-pool-react cycle can be repeated at multiple steps in the chemical synthesis scheme, generating complex final mixtures. Deconvolution of these complex pools to identify lead compounds can be done using iterative screening and resynthesis of smaller libraries. However, this can be time consuming. Therefore, it is preferable to develop encoded libraries where the library is synthesized on beads. The chemical history of each bead is recorded by cosynthesis of an easily analyzable "tag" on each bead . Genetic algorithms can also be use in the design of the combinatorial library.

Figure 7:
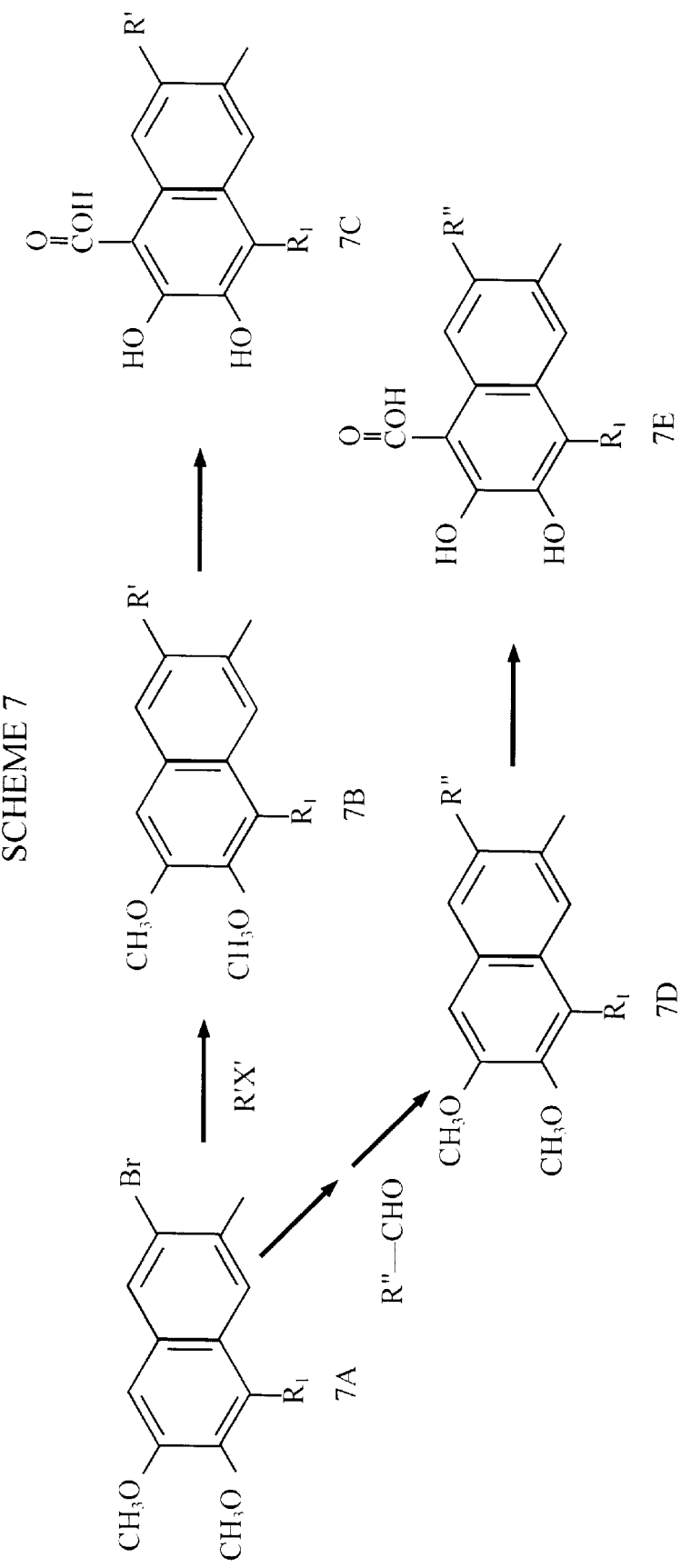
FIG. 7 illustrates a method for making compounds of the present invention.

The rationale for synthesis and screening of very complex mixtures is to increase the probability that one or more high affinity ligand is present in the mixture, thereby improving the chances of identiflying a lead compound. The present invention's method for making dehydrogenase inhibitors represents a different situation since these already are lead compounds. Therefore, the combinatorial library method of the present invention uses screening to identify specific dihydroxynaphthoic acids that exhibit selectivity for the nicotinamide site of a target dehydrogenase. These lead compounds can then be selectively modified to develop potent selective inhibitors. By incorporating a substrate analog into a hydroxynaphthoic acid at position 4, 5, 6, 7, or 8 the combinatorial library method of the present invention is able to produce a Pan-Active Site Inhibitor. A number of the reactions shown in schemes 1 through 6 can be used in the combinatorial library method of the present invention as shown in scheme 7 in FIG. 7. Bromide (7A) represents a family of common intermediates with different $R_1$ groups at the 4-position (schemes 1 and 2). Each of these bromides can be modified with mixtures of alkylhalides (R'X') or with mixtures of substituted benzaldehydes (R"CHO) to form libraries of dihydroxynaphthoic acids with alkyl (7C) or aralkyl (7E) groups at the 7-position. These libraries can be small libraries or complex libraries, depending on the complexity of bromide (7A), R'X', and R"CHO. The essential reactions of bromides (7A) with R'X' or R"CHO, involving initial reaction of 7A with n-butyllithium, are quantitative. The same is true for a number of reactions in schemes 1 through 6 that involve Grignard reactions. Thus, there are multiple points where synthesis of mixtures is feasible. Therefore, scheme 7 is representative of this approach to production of limited sized libraries.

The invention will now be described by way of example. The following examples are illustrative and are not meant to limit the scope of the invention which is set forth by the appended claims.

EXAMPLES

Figure 8:
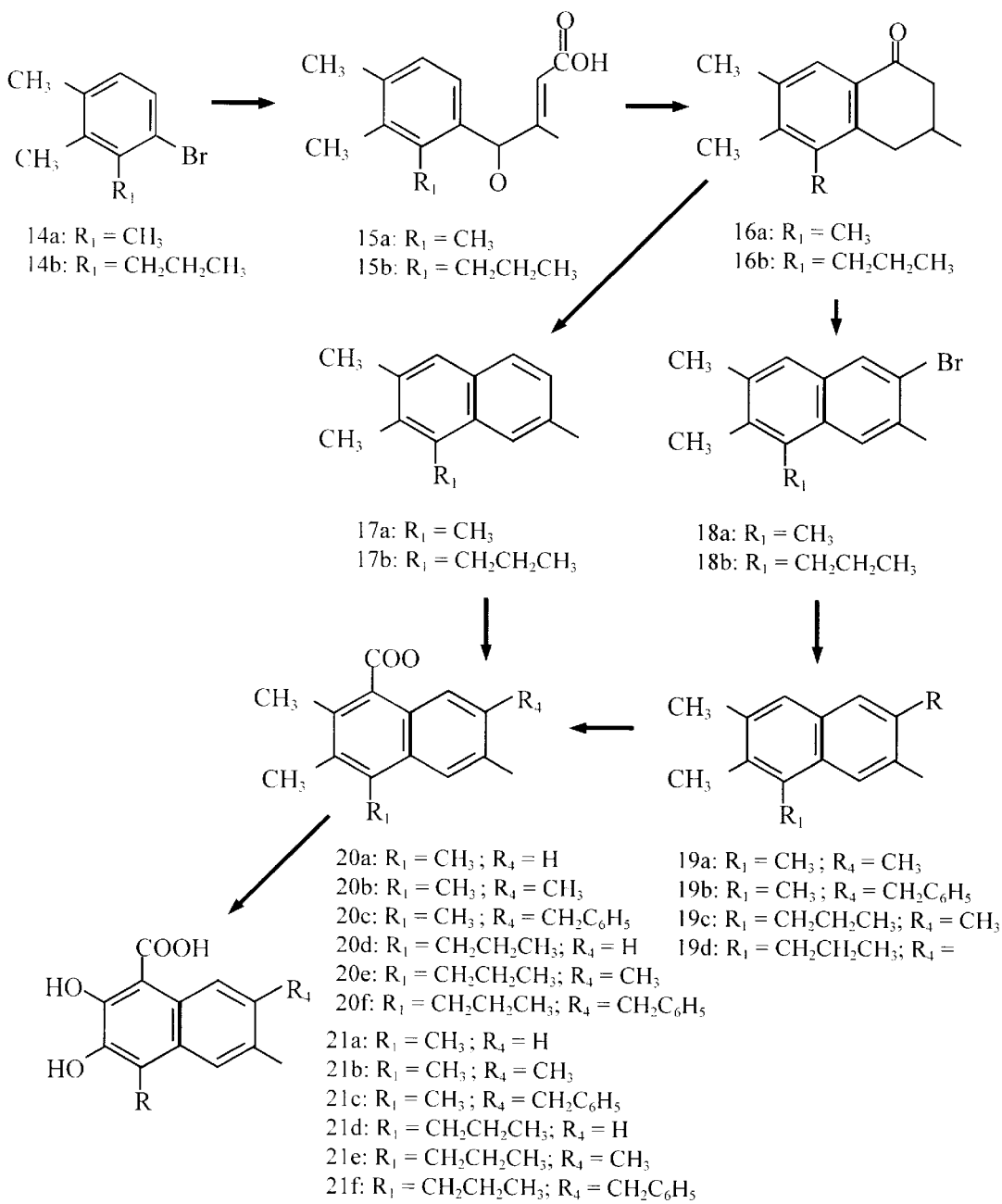
FIG. 8 illustrates methods for making compounds of the present invention.

The syntheses of compounds 21a–21f and 25a–25g of the present are outlined in scheme 8 of FIG. 8 and scheme 9 of FIG. 9, respectively. Synthetic scheme 8 features the incorporation of the carbon atoms for the second ring of the naphthalene system in one step by the reaction of the Grignard reagent formed from 1-bromo-3,4-dimethoxy-2-methylbenzene (14a) and 1-bromo-3,4-dimethoxy-2-n-propylbenzene(14b) with ethyl 3-methyl-4-oxobut-2-enoate. These precursors are readily prepared from commercially available starting materials using a procedure described in Royer et al., "*Synthesis and Anti-HIV Activity of 1,1'-Dideoxygossypol and Related Compounds*", J. Med. Chem. 1995, 38, 2427–2432. Because the esters were difficult to reduce they were saponified, and the acids 15a and 15b were hydrogenolyzed and reduced. The resulting carboxylic acids were cyclized with polyphosphoric ester to give tetralones 16a and 16b. The ketone functional groups of 16a and 16b were reduced with sodium borohydride, and the intermediate alcohols dehydrated on acidic workup to form alkenes which were dehydrogenated with DDQ to form the naphthalenes 17a and 17b. Addition of bromine to the alkenes formed dibromides which were immediately dehydrohalogenated with DMF to form vinyl bromides which were dehydrogenated with DDQ to afford the bromonaphthalenes 18a and 18b. Compounds 18a and 18b were reacted with n-butyl lithium and benzaldehyde to form the benzylic alcohols which were hydrogenolyzed with Pd/C in ethanol to form 19b and 19d. Formation of 19a and 19c was accomplished by reaction of 18a and 18b with n-butyl lithium and methyl iodide. Carbonyl groups were introduced to compounds 17a, 17b, and 19a–19d by formylation with titanium tetrachloride and dichloromethyl methyl ether. Oxidation of the aldehyde groups with sodium hypochlorite formed the carboxylic acids 20a–20f. The methyl groups were removed from the phenolic ethers with boron tribromide to form compounds 21a–21f. Scheme 9 outlines the syntheses of 25a–25g. The precursor compound 22a was prepared from 2-isopropyl phenol using procedures described in Royer et al., ( "*Synthesis and Anty-HIV Activity of 1,1'-Dideoxygossypol and Related Compounds*", J. Med. Chem. 1995, 38, 2427–2432). The transformations to form compounds 23a–23g, 24a–24g, and 25a–25g were accomplished using the same procedures used for the corresponding steps in scheme 8.

Inhibition of Parasite Lactate Dehydrogenase (pLDH) and Human Lactate Dehydrogenases (LDH-H and LDH-M) by Derivatives of 8-Deoxyhemigossylic Acid.

The inhibition of pLDH, LDH-H and LDH-M by 8-deoxyhemigossylicacid (13)

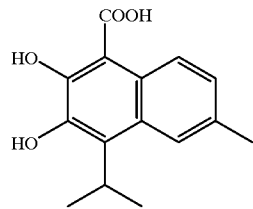

13 the reference compound for these studies, is summarized in Table 1 of FIG. 10. Compound 13 is nonselective in its inhibiton of pLDH and LDH-M, with dissociation constants in the low μmolar range. By comparison, the dissociation constant for inhibition of LDH-H is 30 fold higher than for LDH-M. The inhibition of these three LDH by 13 is competitive with the binding of NADH.

The first series of derivatives of 13 addressed the question whether addition of groups at the 7-position has any effect on binding, in view of the fact that this is the coupling position in the gossypol series and in view of the similar inhibitory properties of 13 and its dimer against pLDH and LDH-M. Compounds 25a and 25b (Table 1) show the effects of methyl or benzyl groups in the 7-position on inhibition of LDH. There is little change in the dissociation constants by introduction of a methyl group. Introduction of a benzyl group results in markedly stronger inhibition of LDH-M and LDH-H but not of pLDH. Surprisingly, however, introduction of a substituted benzyl group has a major effect on all three LDH; the p-trifluoromethylbenzyl derivative (25c, Table 1) is highly selective in favor of pLDH ($K_i$=0.2 μM) compared to either human LDH. Clearly, introduction of the appropriate group at the 7-position can provide selective inhibitors of pLDH.

The second series of compounds related to 13 addressed the question whether modification of the alkyl group in the 4-position affects inhibition of LDH. Two groups of compounds were compared, one with methyl at the 4-position and one with n-propyl at the 4-position, both groups of compounds containing hydrogen, methyl, or benzyl at the 7-position. The results are shown in Table 1. For the 4-methyl derivatives (21a, 21b, and 21c, Table 1), there is selectivity for pLDH and LDH-M compared to LDH-H, and affinity increases with the introduction of groups at the 7-position for all three LDH, especially for LDH-M. For the 4-n-propyl derivatives (21d, 21e, and 21f, Table 1), the presence of the n-propyl group at the 4-position has a marked effect both on affinity and on selectivity. Compound 21e exhibits 190 fold selectivity for LDH-M compared to LDH-H. The most potent inhibitor of the compounds tested in this study is 25d which inhibits LDH-M, $K_D$=30 nM. Thus both the 4-position and the 7-position represent sites for modification of the dihydroxynaphthoic acid backbone in the development of LDH inhibitors.

Discussion

The mechanism of NADH reduction of pyruvate to lactate catalyzed by LDH is thought to involve direct hydride transfer of the pro-R ($H_A$) $C_4$-hydrogen from the reduced nicotinamide ring of NADH to the ketone of pyruvate to form L-lactate. In this mechanism, the ordered formation of the LDH-NADH binary complex and LDH-NADH-pyruvate ternary complex is followed by rate determining closure of a substrate specificity loop to encase the reactants in a desolvated environment before hydride transfer occurs. Hydride transfer is facilitated by the D168/H195 proton donor dyad which transfers a proton to the ketone functional group of pyruvate in concert with hydride transfer, a process that is also facilitated by polarization of the ketone group by R109. R171 acts to anchor the substrate through interaction with the carboxylate group of pyruvate. These catalytic residues are conserved in all LDH.

The unique structural features of pLDH that separate it from human LDH as well as from all other known LDH involve residues both at the cofactor and substrate sites. Residues 98–109 of human LDH-H and LDH-M ([98]AGVRQQEGESRL) define the substrate specificity loop. This sequence is quite highly conserved in all other known LDH, except pLDH where not only the sequence differs but there is also a 5 amino acid insert from residues 104 to 108

([98]AGFTKAPGKSDKEWNRD) which forms an extended specificity loop. The recent crystal structure of the pLDH-NADH-oxamate ternary complex described a closed loop structure with a cleft at the active site which is not present in other LDH. Nevertheless, in spite of these unique structural features of pLDH, this LDH exhibits high specificity for pyruvate. Additional residues that are conserved in other LDH but differ in pLDH include S163, I250 and T246. In most LDH, the nitrogen of the carboxamide group of NADH is H-bonded to the oxygen of S163, whereas in pLDH residue 163 is leucine. In addition, I250 normally provides a hydrophobic sidechain that stacks against the nicotinamide ring; in pLDH residue 250 is proline. T246, which is adjacent to both the nicotinamide group and the substrate in the ternary complex of most LDH, is replaced by proline in pLDH. All of these unique features of pLDH suggest that the active site of pLDH may be a selective drug target.

The results of the present study demonstrate that substituted dihydroxynaphthoic acids structurally related to 8-deoxyhemigossylic acid (13) can be developed that are selective inhibitors of pLDH compared to human LDH and that these inhibitors appear to be competitive with cofactor binding. Compound 25c with a p-trifluoromethylbenzyl moiety at the 7-position of 13 shows 75 and 400 fold selectivity for pLDH over LDH-M and LDH-H, respectively. Surprisingly, however, some of these substituted dihydroxynaphthoic acids are highly selective for LDH-M over LDH-H, in spite of the high sequence homologies of these two human LDH. Generally, these inhibitors show higher affinities for LDH-M compared to LDH-H, with selectivities ranging from 5 to 190 fold.

Figure 11B:
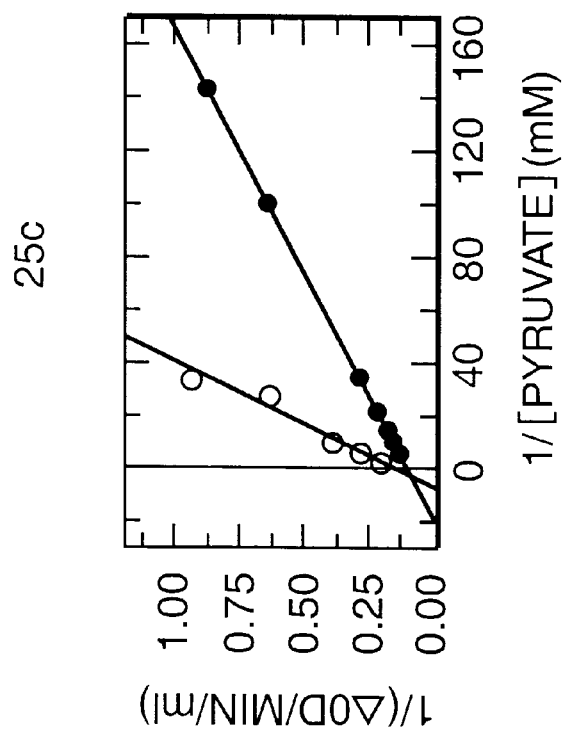
FIGS. 11A and 11B illustrate the inhibition of pLDH by 7-(p-trifluoromethylbenzyl)-8-deoxyhemigossylicacid (25c)
Figure 11A:
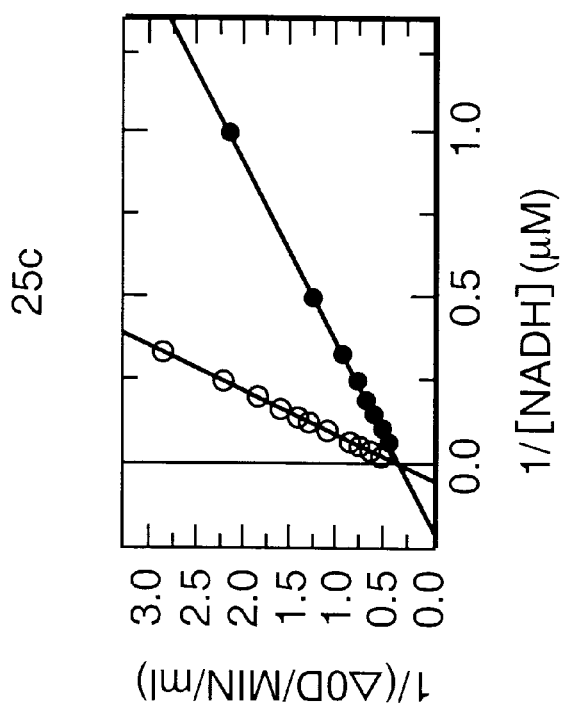
Figure 12B:
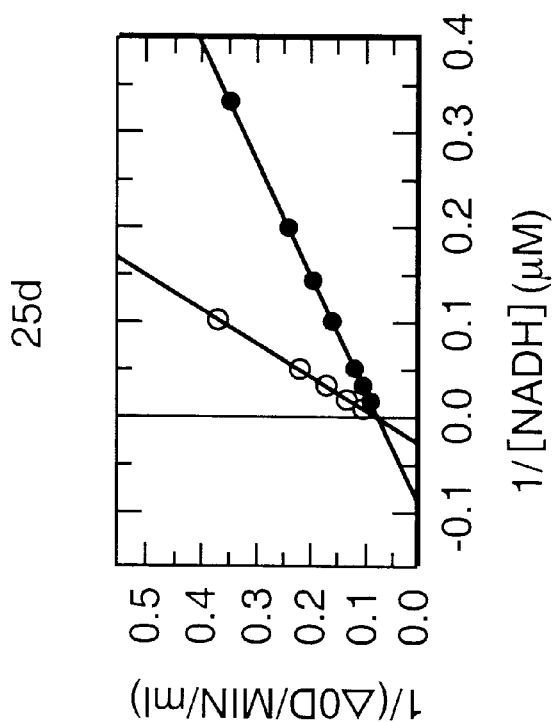
FIGS. 12A and 12B illustrates the inhibition of pLDH-$M_4$ by 2,3-dihydroxy-6-methyl-7-(p-methylbenzyl)-4-(1-methylethyl)-1-naphthoicacid (25d)
Figure 12A:
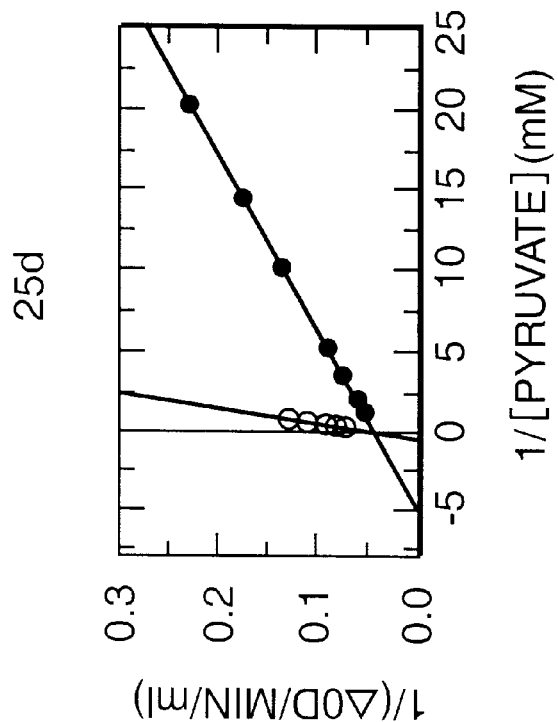

The compounds in Table 1 are competitive inhibitors of cofactor binding, as shown in FIGS. 11a and 12a. Inhibition with respect to substrate binding is generally mixed, but sometimes appears competitive, as shown in FIGS. 11b and 12b for inhibition of pLDH by 25c. These kinetic studies raise the question whether inhibition of LDH by substituted dihydroxynaphthoic acids involves complexation at both the cofactor and substrate binding sites and whether this can be exploited to develop selective dehydrogenase inhibitors.

Experimental Section

Chemical Synthesis. Reagent quality solvents were used without further purification. THF and ether were distilled from calcium hydride. 1-Bromo-3,4-dimethoxy-2-methylbenzene (14a) and 1-bromo-3,4-dimethoxy-2-n-propylbenzene(14b) were synthesized from o-cresol and 2-n-propylphenol respectively according to published procedures (14). Melting points were determined with a VWR Scientific Electrothermal capillary melting point apparatus and are uncorrected. NMR spectra were recorded on a Bruker AC250 NMR spectrometer in $CDCL_3$, unless otherwise stated. Chemical shifts are in ppm relative to TMS.

General Procedure for Removing the Methyl Groups from Phenolic Methyl Ethers with Boron Tribromide. The procedure for removal of methyl groups was identical to that described previously.

General Procedure for Formylation and Oxidation to Form Carboxylic Acids. A reaction mixture with 1 mmol of the compound to be formylated and 2.6 mmol of dichloromethyl methyl ether in 20 mL of dichloromethane under nitrogen was cooled in an ice bath. Titanium tetrachloride (1.5 mmol) was added slowly with stirring. The mixture was allowed to come to ambient temperature and was stirred for 2 h. The mixture was added with stirring to 100 g of ice with 10 mL of 6 M HCl, and the organic layer was washed with water and brine and dried over magnesium sulfate. Filtration and evaporation of the solvent gave a crude oil which was dissolved in 15 mL of acetonitrile and cooled in an ice bath. Sodium dihydrogen phosphate (0.2 mmol) and 30% hydrogen peroxide (1.1 mmol) were added followed by 1.4 mmol of sodium chlorite dissolved in 5 mL water. The reaction mixture was stirred at ambient temperature for 2 h and then poured onto 100 g of ice containing 10 mL of 6 M HCl and extracted with ether. The ether layer was washed with water and brine and dried over magnesium sulfate.

4-[3,4-Dimethoxy-2-methylphenyl]-3-methylbutanoicAcid (15a). Compound 14a (12.0 g, 51.9 mmol) was added to magnesium turnings (1.26 g, 52.1 mmol) in 100 mL dry THF in a 250 mL ground glass Erlenmeyer flask equipped with a reflux condenser and magnetic stirrer. The mixture was refluxed with stirring for 1 h, cooled to 0° C., and added dropwise to 3-methyl-4-oxobut-2-enoate(7.39 g, 52.1 mmol) in 25 mL of dry THF at 0° C. The mixture was stirred at ambient temperature for 1 h and poured onto 100 g ice and 25 mL of 6 M HCl. The organic layer was extracted into ether, washed with water and brine, dried over magnesium sulfate and filtered. The ether was removed by rotary evaporation to give 12.3 g (41.8 mmol, 80% yield) of ester as a crude oil which was dissolved in 100 mL of ethanol with 4.70 g of KOH. Water, 20 mL, was added, and the mixture was refluxed for 3 h. The mixture was poured onto 100 g ice and and 25 mL 6 M HCl and stirred. The white solid was filtered, washed with water, dried and recrystallized from ethyl acetate to give 10.0 g (37.5 mmol, 90% yield) of acid: mp 174–176° C. $^1$H NMR:(ppm) 6.69 (d, 1H), 6.74 (d, 1H), 6.32 (s, 1H), 5.32 (s, 1H), 3.86 (s, 3H), 3.79 (s, 3H), 2.34 (s, 3H), 2.00 (s, 3H), 1.60 (s, 1H). Anal. ($C_{14}H_{18}O_5$) C,H. The acid (10.0 g, 37.6 mmol) in 100 mL of acetic acid was hydrogenated on a Parr hydrogenator with 0.4 g of 10% palladium on carbon and 60 psi hydrogen pressure at 60° C. for 20 h. The reaction mixture was vacuum filtered through celite, and the celite was washed with ether. The solvent was evaporated in a fume hood, and the residual oil was distilled bulb to bulb (170° C., 1 Torr Hg) to give 7.5 g (29.7 mmol, 79% yield) of 15a as an amber oil which crystallized on standing to form colorless crystals: mp 84–86° C. $^1$H NMR:(ppm) 6.78 (d, 1H), 6.67 (d, 1H), 3.83 (s, 3H), 3.77 (s, 3H), 2.62–2.33 (mult, 5H), 2.22 (s, 3H), 0.992 (d, 3H). Anal. ($C_{14}H_{20}O_4$) C,H.

4-[3,4-Dimethoxy-2-n-propylphenyl]-3-methylbutanoicAcid (15b). Compound 14b (10.0 g, 38.6 mmol) and ethyl bromide (0.6 g, 5.5 mmol) were added to magnesium turnings (1.2 g, 49.4.mmol) in 100 mL of dry THF in a 250 mL ground glass Erlenmeyer flask and was refluxed 1 h with stirring. After cooling, the mixture was added dropwise to 3-methyl-4-oxobut-2-enoate (6.90 g, 48.5 mmol) in 25 mL of dry THF at 0° C. The mixture was stirred at ambient temperature for 1 h and poured onto 100 g ice and 25 mL of 6 M HCl. The organic layer was extracted into ether, washed with water and brine, and dried over magnesium sulfate. The ether was evaporated to give 10.6 g (32.9 mmol, 85% yield) of ester as a crude oil which was dissolved in 100 mL of ethanol with 4.50 g of KOH. Water, 20 mL, was added, and the mixture was refluxed for 3 h, then poured onto 100 g of ice and 25 mL of 6 M HCl and stirred. The semi-solid was extracted with ether, washed with water and brine, and dried over magnesium sulfate. Filtration and evaporation of the ether gave 9.20 g (31.3 mmol, 95% yield) of acid as a viscous oil. The acid (9.20 g, 31.3 mmol) in 100 mL of acetic acid was hydrogenated on a Parr hydrogenator with 0.4 g of 10% palladium on carbon and 60 psi hydrogen pressure at 60° C. for 24 h. The reaction mixture was vacuum filtered through celite, and the celite was washed with ether. The solvent was evaporated in a fume hood, and the residual oil was distilled bulb to bulb (180° C., 1 Torr) to give 7.46 g (26.6 mmol, 85% yield) of 15b as a pale yellow oil. $^1$H NMR:(ppm) 6.77 (d, 1H), 6.68 (d, 1H), 3.79 (s, 3H), 3.77 (s, 3H), 2.74–2.08 (m, 7H), 1.50 (sex, 2H), 0.96 (t, 3H), 0.94 (d, 3H). Anal. ($C_{16}H_{24}O_4$) C,H.

3,4-Dihydro-6,7-dimethoxy-3,5-dimethyl-1(2H)-naphthalenone (16a). Compound 15a (7.0 g, 27.7 mmol) was added to 35 g of polyphosphoric ester in 100 mL of methylene chloride and refluxed for 1 h. The reaction mixture was poured onto ice, stirred to hydrolyze the polyphosphoric ester, and the resulting solid was filtered and recrystallized from methanol to give 5.4 g (23.0 mmol, 83% yield) of 16a as white plates: mp 106–108° C. $^1$H NMR: (ppm) 7.48 (s, 1H), 3.89 (s, 3H), 3.84 (s, 3H), 2.95–2.28 (mult, 5H), 2.22 (s, 3H), 1.18 (d, 3H). Anal. ($C_{14}H_{18}O_3$) C,H.

3,4-Dihydro-6,7-dimethoxy-3-methyl-5-n-propyl-1(2H)-naphthalenone (16b). Compound 15b (7.0 g, 25 mmol) was added to 35 g of polyphosphoric ester in 100 mL of methylene chloride and refluxed for 1 h. The reaction mixture was poured onto ice, stirred, and extracted with ether. The ether was evaporated, and the residual oil was chromatographed on silica gel using ethyl acetate/hexane to give 5.63 g (21.5 mmol, 86% yield) of 16b as white crystals: $^1$H NMR:(ppm) 7.49 (s, 1H), 3.89 (s, 3H), 3.87 (s, 3H), 3.00–2.23 (mult, 7H), 1.50 (mult, 2H), 1.15 (d, 3H), 1.01 (t, 3H). Anal. ($C_{16}H_{22}O_3$) C,H.

2,3-Dimethoxy-1,7-dimethylnaphthalene (17a). Compound 16a (4.5 g, 19.2 mmol) was dissolved in 20 mL of 2-propanol, sodium borohydride (1.08 g, 28.8 mmol) was added, and the mixture was stirred at reflux for 1 h. The cooled solution was acidified by dropwise addition of 6 M HCl with stirring, then refluxed for 1 h, poured onto ice and extracted with ether. The ether layer was washed with water and brine and dried over magnesium sulfate. The ether was removed by rotary evaporation, and the residue was distilled bulb to bulb (170° C., 1 Torr) to give 3.31 g (15.2 mmol, 79% yield) of alkene which crystallized on standing. $^1$H NMR:(ppm) 6.50 (s, 1H), 6.31 (mult, H), 5.81 (mult, 1H), 3.83 (s, 3H), 3.77 (s, 3H), 2.84–2.23 (mult, 3H), 2.19 (s, 3H), 1.10 (d,3H). Anal. ($C_{14}H_{18}O_2$) C,H. A mixture of alkene (1.95 g, 8.93 mmol) in 25 mL of benzene and 2,3-dichloro-5,6-dicyano-1,4-benzoquinone(2.03 g, 8.93 mmol) was stirred for 2 h, and the resulting mixture was filtered through a short column of alumina. The solvent was evaporated, and the residual oil was purified by silica column chromatography with dichloromethane. Removal of solvent provided 1.66 g of 17a (7.67 mmol, 86% yield) as colorless crystals: mp 68–69° C. $^1$H NMR:(ppm) 7.63 (s, 1H), 7.59 (d, 1H), 7.21 (d, 1H), 6.99 (s, 1H), 3.93 (s, 3H), 3.83 (s, 3H), 2.56 (s, 3H), 2.49 (s, 3H). Anal. ($C_{14}H_{16}O_2$) C,H.

2,3-Dimethoxy-7-methyl-1-n-propylnaphthalene(17b). Compound 16b (5.00 g, 19.1 mmol) was dissolved in 20 mL of 2-propanol, sodium borohydride (1.08 g, 28.8 mmol) was added, and the reaction mixture was stirred with refluxing for 1 h. After cooling, the mixture was acidified by dropwise addition of 6 M HCl with stirring. The acidified mixture was refluxed for 1 h, poured onto ice and extracted with ether. The ether extract was washed with water and brine and was dried over magnesium sulfate. The ether was removed by rotary evaporation, and the residue was distilled bulb to bulb (190° C., 1 Torr) to give 4.46 g (18.1 mmol, 95% yield) of an alkene. $^1$H NMR:(ppm) 6.51 (s, 1H), 6.31 (dd,1H), 5.80 (dd, 1H), 3.81 (s, 3H), 3.80 (s, 3H), 2.86–2.35 (mult, 5H), 1.50 (m, 2H), 1.10 (d, 3H), 0.99 (t, 3H). The alkene (4.46 g, 18.1 mmol) was dissolved in 25 mL of benzene and was treated while stirring with 2,3-dichloro-5,6-dicyano-1,4-benzoquinone (4.10 g, 18.0 mmol) and was stirred an additional 2 h. The reaction mixture was filtered through a short column of alumina and washed with benzene. The solvent was evaporated, and the residual oil was purified by silica column chromatography using dichloromethane to give 4.24 g (17.4 mmol, 96% yield) of 17b as an oil. $^1$H NMR:(ppm) 7.64 (s, 1H), 7.60 (d, 1H), 7.21 (d, 1H), 7.01 (s, 1H), 3.95 (s, 3H), 3.87 (s, 3H), 3.01 (t, 2H), 2.50 (s, 3H), 1.67 (m, 2H), 1.06 (t, 3H). Anal. ($C_{16}H_{20}O_2$) C,H.

6-Bromo-2,3-dimethoxy-1,7-dimethylnaphthalene(18a). Compound 16a (4.5 g, 19.2 mmol) was converted into the alkene as described in the synthesis of 17a. The alkene (1.48 g, 6.78 mmol) was dissolved in 100 mL of dry dichloromethane, and bromine (1.08 g, 6.78 mmol) in 5 mL dichloromethane was added dropwise with stirring over a 15 min period. The solvent was evaporated, and the residue was taken up in 25 mL of DMF and warmed to 60–70° C. for 1 h. The reaction mixture was poured onto ice and stirred. The solid was filtered, dried and recrystallized from petroleum ether to give 1.51 g (5.08 mmol, 75% yield) of colorless crystals: mp 75–76° C. $^1$H NMR:(ppm) 6.65 (s, 1H), 6.43 (s, 1H), 3.82 (s, 3H), 3.77 (s, 3H), 3.03–2.62 (mult, 3H), 2.18 (s, 3H), 1.11 (d, 3H). Anal. ($C_{14}H_{17}BrO_2$) C,H. The vinylic bromide (1.51 g, 5.08 mmol) was dissolved in 25 mL of benzene, and 2,3-dichloro-5,6-dicyano-1,4-benzo-quinone (1.14 g, 5.02 mmol) was added with stirring, and stirring was continued for 2 h. The reaction mixture was filtered through a short column of alumina and eluted with benzene. The solvent was evaporated, and the residual oil was purified by silica column chromatography using dichloromethane to give 1.24 g (4.21 mmol, 83% yield) of 18a as colorless crystals: mp 96–97° C. $^1$H NMR:(ppm) 7.89 (s, 1H), 7.67 (s, 1H), 6.89 (s, 1H), 3.94 (s, 3H), 3.84 (s, 3H), 2.54 (s, 6H). Anal. ($C_{14}H_{15}BrO_2$) C,H.

6-Bromo-2,3-dimethoxy-7-methyl-1-n-propylnaphthalene(18b). Compound 16b (3.5 g, 13.4 mmol) was reduced with sodium borohydride as described in the synthesis of 17b. The alkene (2.5 g, 10.1 mmol) was dissolved in 100 mL of dry dichloromethane, and bromine (1.62 g, 10.1 mmol) in 5 mL dichloromethane was added dropwise with stirring over a period of 15 min. The solvent was evaporated, and the residue was taken up in 15 mL of DMF and warmed to 60–70° C. for 1 hr. The reaction mixture was poured onto ice and stirred, after which the solid was filtered, dried and recrystallized from petroleum ether to give 2.46 g (7.56 mmol, 75% yield) of white crystals. The vinylic bromide (1.23 g, 3.78 mmol) was dissolved in 25 mL of benzene, and 2,3-dichloro-5,6-dicyano-1,4-benzoquinone(857 mg, 3.78 mmol) was added slowly with stirring, followed by continued stirring for 2 h. The reaction mixture was filtered through a short column of alumina and eluted with benzene. The solvent was evaporated, and the residual oil was purified by silica column chromatography using dichloromethane to give 1.04 g (3.21 mmol, 85% yield) of 18b as colorless crystals, mp 64–66° C. $^1$H NMR:(ppm) 7.90 (s, 1H), 7.69 (s, 1H), 6.91 (s, 1H), 3.94 (s, 3H), 3.87 (s, 3H), 2.99 (t, 2H), 2.54 (s, 3H), 1.66 (m, 2H), 1.05 (t, 3H). Anal. ($C_{16}H_{19}BrO_2$) C,H.

2,3-Dimethoxy-1,6,7-trimethylnaphthalene(19a). Compound 18a (646 mg, 2.19 mmol) in 25 mL of dry ether was cooled to 0° C. under nitrogen. n-Butyllithium (2.50 mmol) was added as a solution in hexane. The mixture was stirred for 15 min at 0° C., and then methyl iodide (0.38 g, 3.0 mmol) was added. The mixture was stirred at ambient temperature under nitrogen for 1 h. The reaction mixture was poured onto 10 g of ice containing 2 mL of HCl, and the organic layer was separated, washed with water and brine and dried over magnesium sulfate. After filtration, the ether was evaporated to give an oil which was purified by silica column chromatography using dichloromethane to give 426 mg (1.84 mmol, 84% yield) of 19a as buff crystals, mp 59–60° C. $^1$H NMR:(ppm) 7.59 (s, 1H), 7.44 (s, 1H), 6.93 (s, 1H), 3.93 (s, 3H), 3.83 (s, 3H), 2.56 (s, 3H), 2.41 (s, 3H), 2.38 (s, 3H). Anal. ($C_{15}H_{18}O_2$) C,H.

6-Benzyl-2,3-dimethoxy-1,7-dimethylnaphthalene (19b). Compound 18a (570 mg, 1.93 mmol) in 25 mL of dry ether was cooled to 0° C. under nitrogen. n-Butyllithium (2.2 mmol) was added as a solution in hexane. The mixture was stirred for 15 min at 0° C., and then benzaldehyde (265 mg, 2.5 mmol) was added. The mixture was stirred at ambient temperature under nitrogen for 1 h. The reaction mixture was poured onto ice containing HCl and stirred for 1 h. The mixture was filtered to give a buff solid. $^1$H NMR:(ppm) 7.85 (s, 1H), 7.60 (s, 1H), 7.34–7.25 (m, 5H), 7.03 (s, 1H), 6.09 (s, 1H), 3.94 (s, 3H), 3.84 (s, 3H), 2.55 (s, 3H), 2.34 (s, 3H), 2.28 (brs, 1H, disappears upon shaking with $D_2O$). The alcohol was dissolved in ethanol and hydrogenated on a Parr hydrogenator with 10% palladium on carbon and 60 psi hydrogen pressure at room temperature for 2 h. The reaction mixture was vacuum filtered through celite, and the celite was washed with ether. The solvent was removed, and the residual oil was purified by silica column chromatography using dichloromethane to give 522 mg (1.70 mmol, 88% yield) of 19b as a crystalline solid, $^1$H NMR:(ppm) 7.63 (s, 1H), 7.41 (s, 1H), 7.30–7.14 (m, 5H), 6.95 (s, 1H), 4.11 (s, 2H), 3.93 (s, 3H), 3.84 (s, 3H), 2.56 (s, 3H), 2.36 (s, 3H).

2,3-Dimethoxy-6,7-dimethyl-1-n-propylnaphthalene (19c). Compound 18b (700 mg, 2.16 mmol) in 25 mL of dry ether was cooled to 0° C. under nitrogen. n-Butyllithium (3.0 mmol) was added as a solution in hexane. The mixture was stirred for 15 min at 0° C., and then methyl iodide (0.38 g, 3 mmol) was added. The mixture was stirred at ambient temperature under nitrogen for 1 h. The reaction mixture was acidified, and the organic layer was separated, washed with water and brine, and dried over magnesium sulfate. After filtration, the ether was evaporated to give an oil which was purified by silica column chromatography to give 446 mg (1.73 mmol, 80% yield) of 19c as an amber oil. $^1$H NMR:(ppm) 7.89 (s, 1H), 7.44 (s, 1H), 6.93 (s, 1H), 3.92 (s, 3H), 3.86 (s, 3H), 3.01 (t, 2H), 2.40 (s, 3H), 2.37 (s, 3H), 1.67 (m, 2H), 1.05 (t, 3H). Anal. ($C_{17}H_{22}O_2$) C,H.

6-Benzyl-2,3-dimethoxy-7-methyl-1-n-propylnaphthalene(19d). Compound 18b (800 mg, 2.47 mmol) in 25 mL of dry ether was cooled to 0° C. under nitrogen. n-Butyllithium (3.0 mmol) was added as a solution in hexane. The mixture was stirred for 15 min at 0° C., and then benzaldehyde (424 mg, 4 mmol) was added. The mixture was stirred at ambient temperature under nitrogen for 1 h. The reaction mixture was acidified, and the organic layer was separated, washed with water and brine, and was dried over magnesium sulfate. After filtration, the ether was evaporated to give a semi-solid which was dissolved in ethanol and hydrogenated on a Parr hydrogenator with 10% palladium on carbon and 60 psi hydrogen pressure at room temperature for 2 h. The reaction mixture was vacuum filtered through celite, and the celite was washed with ether. The solvent was evaporated, and the residual oil was purified by silica column chromatography using dichloromethane to give 727 mg (2.17 mmol, 88% yield) of 19d as a crystalline solid, mp 83–85° C. $^1$H NMR:(ppm) 7.64 (s, 1H), 7.39 (s, 1H), 7.14–7.29 (m, 5H), 6.95 (s, 1H), 4.09 (s, 2H), 3.91 (s, 3H), 3.86 (s, 3H), 3.01 (t, 2H), 2.36 (s, 3H), 1.68 (m, 2H), 1.05 (t, 3H). Anal. ($C_{23}H_{26}O_2$) C,H.

2,3-Dimethoxy-4,6-dimethyl-1-naphthoic acid (20a). Compound 17a (1.38 g, 6.38 mmol) was formylated by the general procedure for formylation to give 1.51 g (6.18 mmol, 97% yield) of solid aldehyde. $^1$H NMR:(ppm) 10.74 (s, 1H), 9.15 (d, 1H), 7.72 (s, 1H), 7.40 (d, 1H), 4.04 (s, 3H), 3.87 (s, 3H), 2.62 (s, 3H), 2.50 (s, 3H). Oxidation by the general procedure for oxidation gave a solid that was purified by silica column chromatography using dichloromethane to give 1.18 g (4.53 mmol, 72% yield) of 20a as white crystals. $^1$H NMR:(ppm) 8.07 (d, 1H), 7.70 (s, 1H), 7.35 (d, 1H), 4.06 (s, 3H), 3.89 (s, 3H), 2.60 (s, 3H), 2.51 (s, 3H). Anal. ($C_{15}H_{16}O_4$) C,H.

2,3-Dimethoxy-4,6,7-trimethyl-1-naphthoic acid (20b). Compound 19a (317 mg, 1.37 mmol) was formylated by the general procedure for formylation to give 318 mg (1.23 mmol, 89% yield) of solid aldehyde. $^1$H NMR:(ppm) 10.75 (s, 1H), 9.05 (s, 1H), 7.67 (s, 1H), 4.05 (s, 3H), 3.88 (s, 3H), 2.63 (s, 3H), 2.48 (s, 3H), 2.44 (s, 3H). Oxidation by the general procedure for oxidation gave a solid that was purified by silica column chromatography using dichloromethane to give 306 mg (1.12 mmol, 81% yield) of 20b as white crystals, mp 138–140° C. $^1$H NMR:(ppm) 8.08 (s, 1H), 7.68 (s, 1H), 4.07 (s, 3H), 3.89 (s, 3H), 2.61 (s, 3H), 2.44 (s, 6H). Anal. ($C_{16}H_{18}O_4$) C,H.

7-Benzyl-2,3-dimethoxy-4,6-dimethyl-1-naphthoic acid (20c). Compound 19c (250 mg, 0.816 mmol) was formylated by the general procedure for formylation to give 250 mg (0.748 mmol, 92% yield) of solid aldehyde. $^1$H NMR:(ppm) 10.74 (s, 1H), 9.16 (s, 1H), 7.66 (s, 1H), 7.18–7.10 (m, 5H), 4.13 (s, 2H), 4.02 (s, 3H), 3.84 (s, 3H), 2.59 (s, 3H), 2.31 (s, 3H). Oxidation by the general procedure for oxidation gave a solid that was purified by silica column chromatography using dichloromethane to give 207 mg (0.591 mmol, 79% yield) of 20c.

2,3-Dimethoxy-6-methyl-4-n-propyl-1-naphthoic acid (20d). Compound 17b (1.38 g, 6.38 mmol) was formylated by the general procedure for formylation to give 1.51 g (6.18 mmol, 97% yield) of solid aldehyde. Oxidation by the general procedure for oxidation gave a solid that was purified by silica chromatography using dichloromethane to give 1.18 g (4.53 mmol, 72% yield) of 20d as white crystals, mp 123–125° C. $^1$H NMR:(ppm) 8.10 (d, 1H), 7.71 (s, 1H), 7.33 (d, 1H), 4.06 (s, 3H), 3.94 (s, 3H), 3.06 (t, 2H), 2.52 (s, 3H), 1.70 (m, 2H), 1.09 (t, 3H). Anal. ($C_{17}H_{20}O_4$) C,H.

2,3-Dimethoxy-6,7-dimethyl-4-n-propyl-1-naphthoic acid (20e). Compound 19c (317 mg, 1.38 mmol) was formylated by the general procedure for formylation to give 318 mg (1.23 mmol, 89% yield) of solid aldehyde. Oxidation by the general procedure for oxidation gave a solid that was purified by silica column chromatography to give 306 mg (1.12 mmol, 81% yield) of 20e as white crystals.

7-Benzyl-2,3-dimethoxy-6-methyl-4-n-propyl-1-naphthoic acid (20f). Compound 19d (250 mg, 0.816 mmol) was formylated by the general procedure for formylation to give 250 mg (0.748 mmol, 92% yield) of solid aldehyde. Oxidation by the general procedure for oxidation gave 207 mg (0.591 mmol, 79% yield) of 20f as white crystals, mp 143–145° C. $^1$H NMR:(ppm) 8.03 (s, 1H), 7.70 (s, 1H), 7.27–7.10 (m, 5H), 4.15 (s, 2H), 4.05 (s, 3H), 3.93 (s, 3H), 3.05 (t, 2H), 2.34 (s, 3H), 1.69 (m, 2H), 1.08 (t, 3H). Anal. ($C_{24}H_{26}O_4$) C,H.

2,3-Dihydroxy-4,6-dimethyl-1-naphthoic acid (21a). Compound 20a (500 mg, 1.92 mmol) was demethylated by the general procedure for demethylation. The solvent was evaporated, and the product was recrystallized from ether/petroleum ether to give 350 mg (1.51 mmol, 79% yield) of 21a as buff colored crystals. Anal. ($C_{13}H_{12}O_4$) C,H.

2,3-Dihydroxy-4,6,7-trimethyl-1-naphthoic acid (21b). Compound 20b (400 mg, 1.46 mmol) was demethylated, and the product was purified as above to give 270 mg (1.10 mmol, 75% yield) of 21b as buff colored crystals.

7-Benzyl-2,3-dihydroxy-4,6-dimethyl-1-naphthoic acid (21c). Compound 20c (634 mg, 1.81 mmol) was demethylated, and the product was purified as above to give 420 mg (1.30 mmol, 72% yield) of 21c as buff colored crystals, mp 179–180° C. Anal. ($C_{20}H_{18}O_4$) C,H.

2,3-Dihydroxy-6-methyl-4-n-propyl-1-naphthoic acid (21d). Compound 20d (600 mg, 2.08 mmol) was demethylated, and the product was purified as above to give 390 mg (1.50 mmol, 72% yield) of 21d as buff colored crystals, mp 159–160° C. Anal. ($C_{15}H_{16}O_4$) C,H.

2,3-Dihydroxy-6,7-dimethyl-4-n-propyl-1-naphthoic acid (21e). Compound 20e (550 mg, 1.82 mmol) was demethylated, and the product was purified as above to give 380 mg (1.27 mmol, 70% yield) of 21e as buff colored crystals, mp 170–172° C. Anal. ($C_{16}H_{18}O_4$) C,H.

7-Benzyl-2,3-dihydroxy-6-methyl-4-n-propyl-1-naphthoicacid (21f). Compound 20f (634 mg, 1.67 mmol) was demethylated, and the product was purified as above to give 417 mg (1.19 mmol, 71% yield) of 21f as buff colored crystals, mp 183–184° C. $^1$NMR:(ppm, DMSO-$d_6$) 8.63 (s, 1H), 7.61 (s, 1H), 7.27–7.12 (m, 5H), 4.01 (s, 2H), 2.97 (t, 2H), 2.28 (s, 3H), 1.57 (m, 2H), 0.99 (t, 3H). Anal. ($C_{22}H_{22}O_4$) C,H.

2,3-Dimethoxy-6,7-dimethyl-1-(1-methylethyl)-naphthalene(23a). Compound 22a (14) (1.40 g, 4.32 mmol) in 25 mL dry ether was cooled to 0° C. under nitrogen. n-Butyllithium (6.0 mmol) was added as a solution in hexane. The mixture was stirred for 15 min at 0° C., and then methyl iodide (1.14 g, 8.0 mmol) was added. The mixture was stirred at ambient temperature under nitrogen for 1 h, then acidified, and the organic layer was separated, washed with water and brine and dried over magnesium sulfate. After filtration, the ether was evaporated to give an oil which was purified by silica column chromatography using dichloromethane to give 892 mg (3.46 mmol, 80% yield) of 23a as buff colored crystals, mp 75–77° C. $^1$H NMR:(ppm) 7.85 (s, 1H), 7.44 (s, 1H), 6.93 (s, 1H), 3.89 (m, 1H), 3.88 (s, 3H), 3.85 (s, 3H), 2.39 (s, 3H), 2.35 (s, 3H), 1.51 (d, 6H). Anal. ($C_{17}H_{22}O_2$) C,H.

6-Benzyl-2,3-dimethoxy-7-methyl-1-(1-methylethyl)-naphthalene (23b). Compound 22a (1.14 g, 3.86 mmol) in 25 mL of dry ether was cooled to 0° C. under nitrogen. n-Butyllithium (4.5 mmol) was added as a solution in hexane. The mixture was stirred for 15 min at 0° C., and then benzaldehyde (1.06 g, 5.0 mmol) was added. The mixture was stirred at ambient temperature under nitrogen for 1 h. The reaction mixture was acidified, and the organic layer was separated, washed with water and brine, and dried over magnesium sulfate. After filtration, the ether layer was evaporated to give a white solid, mp 163–165° C. $^1$H NMR:(ppm) 7.84 (s, 1H), 7.25–7.34 (m, 6H), 7.03 (s, 1H), 6.08 (s, 1H), 3.93 (s, 3H) 3.91 (m, 1H), 3.88 (s, 3H), 2.34 (s, 3H), 2.25 (broad s, 1H, which disappeared upon shaking with $D_2O$), 1.50 (d, 6H). The alcohol was dissolved in ethanol and hydrogenated on a Parr hydrogenator with 10% palladium on carbon and 60 psi hydrogen pressure at room temperature for 2 h. The reaction mixture was vacuum filtered through celite, and the celite was washed with ether. The solvent was removed to afford a pale yellow solid that was recrystallized from ethyl acetate to give 1.04 g (3.11 mmol, 88% yield) of 23b as a white crystalline solid, mp 159–161° C. $^1$H NMR:(ppm) 7.88 (s, 1H), 7.40 (s, 1H), 7.32–7.15 (m, 5H), 6.96 (s, 1H), 4.09 (s, 2H), 3.93 (s, 3H), 3.87 (s, 3H), 2.37 (s, 3H), 1.50 (d, 6H). Anal. ($C_{23}H_{26}O_2$) C,H.

6-p-Trifluoromethylbenzyl-2,3-dimethoxy-7-methyl-1-(1-methylethyl)-naphthalene (23c). Compound 22a (1.00 g, 3.09 mmol) in 25 mL of dry ether was cooled to 0° C. under nitrogen. n-Butyllithium (4 mmol) was added as a solution in hexane. The mixture was stirred for 15 min at 0° C., and then p-trifluoromethylbenzaldehyde(0.87 g, 5.0 mmol) was added. The mixture was stirred at ambient temperature under nitrogen for 1 h. The reaction mixture was acidified, and the organic layer was separated, washed with water and brine, and dried over magnesium sulfate. After filtration, the ether layer was evaporated to give a semi-solid which was dissolved in ethanol and hydrogenated on a Parr hydrogenator with 10% palladium on carbon and 60 psi hydrogen pressure at room temperature for 2 h. The reaction mixture was vacuum filtered through celite, and the celite was washed with ether. The solvent was removed, and the residual oil was purified by silica column chromatography using dichloromethane to give 1.09 g (2.72 mmol, 88% yield) of 23c as a crystalline solid. $^1$H NMR: (ppm) 7.90 (s, 1H), 7.55 (d, 2H), 7.26 (d, 2H), 6.98 (s, 1H). 4.15 (s, 2H), 3.93 (s, 3H), 3.88 (s, 3H), 3.48 (m, 1H), 2.04 (s, 3H), 1.50 (d, 6H).

2,3-Dimethoxy-6,7-dimethyl-4-(1-methylethyl)-1-naphthoic acid (24a). Compound 23a (550 mg, 2.13 mmol) was formylated by the general procedure for formylation to give 506 mg (1.77 mmol, 83% yield) of solid aldehyde. Oxidation by the general procedure for oxidation gave a solid that was purified by silica column chromatography using dichloromethane to give 450 mg (1.49 mmol, 84% yield) of 24a as white crystals, mp 191–193° C. $^1$H NMR: (ppm) 7.96 (s, 1H), 7.93 (s, 1H), 4.05 (s, 3H), 3.95 (m, 1H), 3.93 (s, 3H), 2.44 (brs, 6H), 1.52 (d, 6H). Anal. ($C_{18}H_{22}O_4$) C,H.

7-Benzyl-2,3-dimethoxy-6-methyl-4-(1-methylethyl)-naphthoic acid (24b). Compound 23b (500 mg, 1.49 mmol) was formylated by the general procedure for formylation to give 446 mg (1.23 mmol, 82% yield) of solid aldehyde. $^1$H NMR:(ppm) 10.75 (s, 1H), 9.16 (s, 1H), 7.93 (s, 1H), 7.32–7.13 (m, 5H), 4.16 (s, 2H), 4.02 (s, 3H), 3.95 (m, 1H), 3.92 (s, 3H), 2.35 (s, 3H), 1.52 (d, 6H). Oxidation by the general procedure described for oxidation gave a solid which was purified by silica column chromatography using dichloromethane to give 391 mg (1.03 mmol, 84% yield) of 24b as white crystals. $^1$H NMR:(ppm) 8.00 (s, 1H), 7.94 (s, 1H), 7.24–7.11 (m, 5H), 4.15 (s, 2H), 4.04 (s, 3H), 3.95 (m, 1H), 3.93 (s, 3H), 2.34 (s, 3H), 1.52 (d, 6H). Anal. ($C_{24}H_{26}O_4$) C,H.

2,3-Dimethoxy-6-methyl-4-(1-methylethyl)-7-p-trifluoromethylbenzyl-1-naphthoic acid (24c). Compound 23c (600 mg, 1.49 mmol) was formylated by the general procedure for formylation to give 526 mg (1.22 mmol, 82% yield) of solid aldehyde. $^1$H NMR:(ppm) 10.74 (s, 1H), 9.18 (s, 1H), 7.97 (s, 1H), 7.49 (d, 2H), 7.22 (d, 2H), 4.19 (s, 2H), 4.02 (s, 3H), 3.90 (m, 1H), 3.91 (s, 3H), 2.30 (s, 3H), 1.50 (d, 6H). Oxidation by the general procedure for oxidation gave a solid which was purified by silica column chromatography to give 458 mg (1.02 mmol, 84% yield) of 24c as white crystals.

2,3-Dihydroxy-6,7-dimethyl-4-(1-methylethyl)-1-naphthoic acid (25a). Compound 24a (450 mg, 1.49 mmol) was demethylated, and the product was recrystallized from ether/petroleum ether to give 302 mg (1.10 mmol, 68% yield) of 25a as buff colored crystals.

7-Benzyl-2,3-dihydroxy-6-methyl-4-(1-methylethyl)-1-naphthoic acid (25b). Compound 24b (652 mg, 1.72 mmol) was demethylated, and the product was recrystallized from ether/petroleum ether to give 416 mg (1.19 mmol, 69% yield) of 25b as buff colored crystals. $^1$H NMR:(ppm) 8.61

(s, 1H), 7.89 (s, 1H), 7.25–7.15 (m, 5H), 6.25 (s, 1H), 4.15 (s, 2H), 3.90 (m, 1H), 2.36 (s, 3H), 1.51 (d, 6H). Anal. ($C_{22}H_{22}O_4$) C,H.

7-p-Trifluoromethylbenzyl-2,3-dihydroxy-6-methyl-4-(1-methylethyl)-1-naphthoic acid (25c). Compound 24c (300 mg, 0.672 mmol) was demethylated, and the product was recrystallized from ether/petroleum ether to give 196 mg (0.47 mmol, 70% yield) of 25c as buff colored needles. $^1$H NMR:(ppm) 8.97 (s, 1H), 7.87 (s, 1H), 7.86 (d, 2H), 7.14 (d, 2H), 6.25 (s, 1H), 4.20 (s, 2H), 3.86 (m, 1H), 2.32 (s, 3H), 1.52 (d, 6H). Anal. ($C_{23}H_{21}F_3O_4$) C,H.

Compounds 25d, 25e, 25f, and 25g were made by procedures similar to that used to make compound 25c.

Purification of Recombinant Parasite Lactate Dehydrogenase.

Recombinant pLDH was produced in *E. coli*, similar to the procedure described by Bzik et al. in "Expression of Plasmodium falciparum Lactate Dehydrogenase in *Escherida coli*." in *Mol. Biochem. Parasitol.*, 1993, 59, 155–166 and was purified by Cibacron blue affinity chromatography and chromatofocusing as described previously. Human LDH-$H_4$ and LDH-$M_4$ were from Sigma.

Enzyme Assays and Kinetics.

LDH activity in the direction of NADH reduction of pyruvate to L-lactate was determined spectrophotometrically in pH 7.5 Tris buffer, 100 mM, containing 10 mM pyruvate and 1 mM NADH, 25° C., 340 nm, $\epsilon=6.2$ mM$^{-1}$ cm$^{-1}$. Michaelis constants were determined by nonlinear regression analysis of initial rate data using the Enzfitter program (Elsevier-Biosoft). $K_i$ values were determined from double reciprocal plots by linear regression analysis.

Those hydroxynaphthoic acids of the present invention which have been structurally designed to occupy the substrate site such as 25c and 25d (see FIG. 9) lead to a Pan-Active Site, potent and selective inhibition as shown in FIGS. 11A, 11B, 12A and 12B. Pan-Active Site inhibitors are defined as inhibitors that occupy all or parts of both the substrate binding site and the cofactor binding site. FIGS. 11A and 11B show that inhibition of pLDH by 7-(p-trifluoromethylbenzyl)-8-deoxyhemigossylicacid (25c) is competitive against both cofactor and substrate. FIGS. 12A and 12B show that inhibition of pLDH-$M_4$ by 2,3-dihydroxy-6-methyl-7-(p-methylbenzyl)-4-(1-methylethyl)-1-naphthoic acid (25d) is competitive against both cofactor and substrate.

Figure 13B:
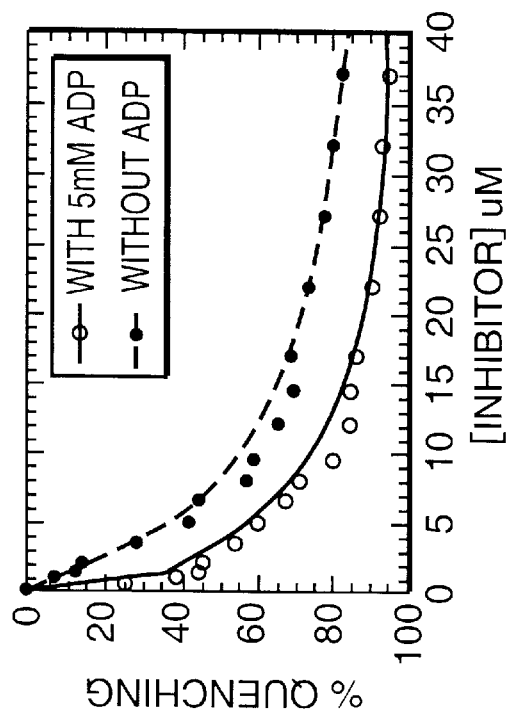
FIG. 13B illustrates the quenching of the intrinsic protein fluorescence of pLDH by a compound of the present invention in the presence and absence of ADP.
Figure 13A:
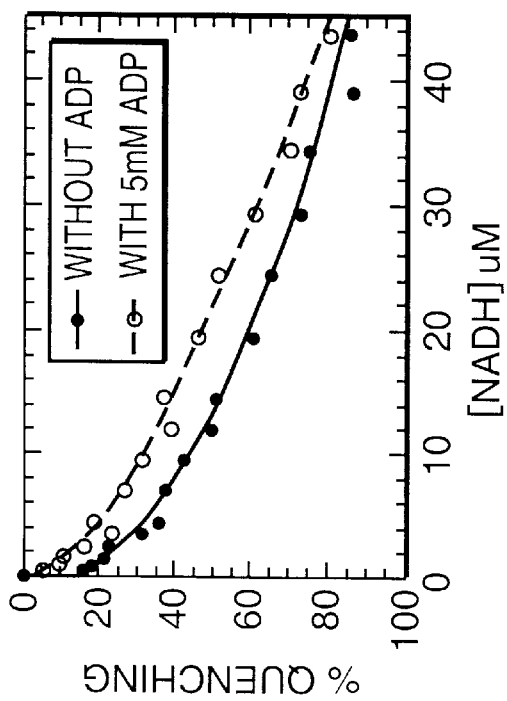
FIG. 13A illustrates the quenching of the intrinsic protein fluorescence of pLDH by NADH in the presence and absence of ADP.

To test the Pan-Active Site inhibitor model for the compounds of the present invention, the binding of dihydroxynaphthoic acids to pLDH and human LDH was examined using fluorescence techniques. The effects of ADP on the binding of inhibitors was compared with the effects of ADP on the binding of NADH to determine which part of the cofactor binding site was the target of the inhibitors. Representative results are shown in FIGS. 13A and 13B for the binding of compound 25c to pLDH. In FIG. 13A is shown the quenching of intrinsic protein fluorescence of pLDH by NADH in the presence or absence of ADP, demonstrating that the presence of ADP competes with the binding of NADH (as shown by the shift to the right of the quenching curve). In FIG. 13B is shown the quenching of pLDH fluorescence by compound 25c in the presence and absence of ADP. The presence of ADP actually enhances the binding of inhibitor (as shown by the shift to the left of the quenching curve). From these results, it is clear that compound 25c is not competing with the ADP part of the NADH binding site, suggesting that the compound 25c binds to the nicotinamide part of the NADH site. The same results were obtained with LDH-$M_4$.

The results described in Table 1 of FIG. 10 and in FIGS. 11A through 13B support the conclusion that substituted dihydroxynaphthoic acids inhibit LDH and pLDH as competitive inhibitors of cofactor binding at the nicotinamide site and are consistent with the idea that inhibition may also involve the substrate site. These results support the concept of Pan Active Site inhibition.

Figure 14B:
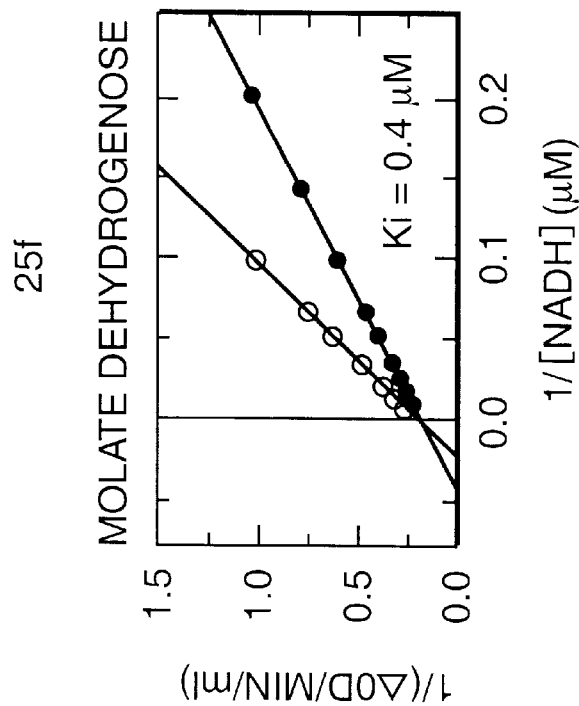
FIGS. 14A, 14B, 14C and 14D illustrate the inhibition of various dehydrogenases by compounds of the present invention.
Figure 14A:
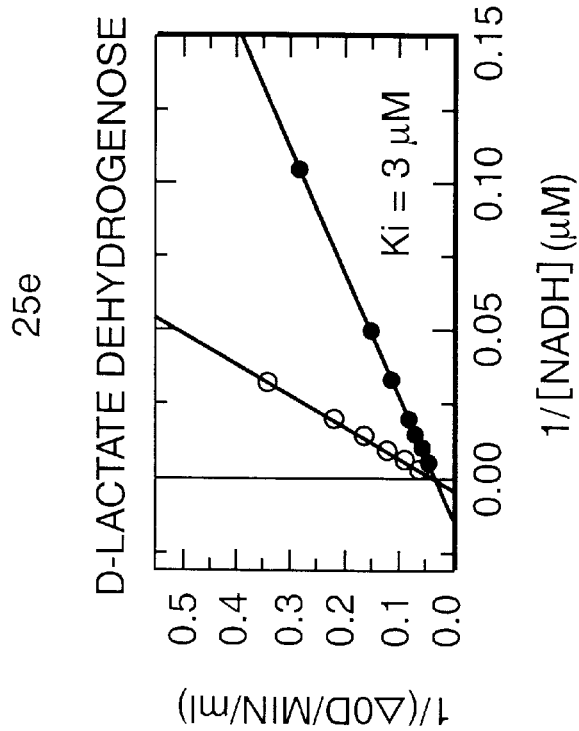
Figure 14D:
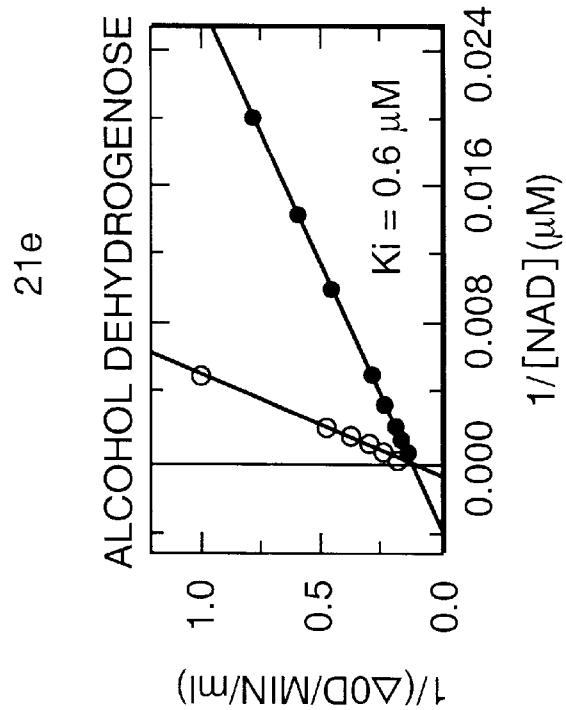
Figure 14C:
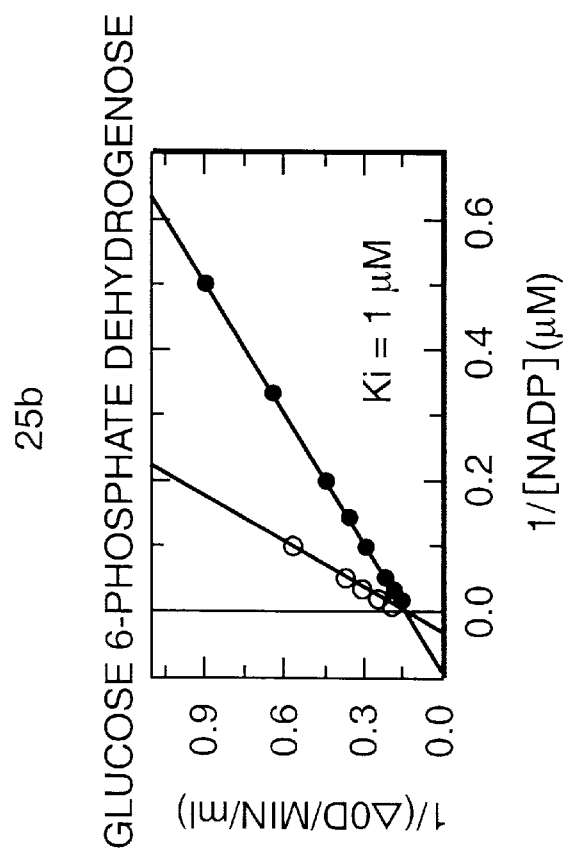

Other studies with other dehydrogenases that contain the classic Rossman fold, in addition to LDH, were carried out to test that inhibition of dehydrogenases by substituted didhydroxynaphthoic acids is not limited to inhibition of LDH. A number of dehydrogenases were examined as shown in FIGS. 14A (2,3-dihydroxy-6-methyl-7-(o-methylbenzyl)-4-(1-methylethyl)-1-naphthoic acid (25e) inhibition D-lactate dehydrogenase), 14B (2,3-dihydroxy-6-methyl-7-(m-methylbenzyl)-4-(1-methylethyl)-1-naphthoic acid (25f) inhibition of malate dehydrogenase), 14C (compound 25b inhibition of glucose 6-phosphate dehydrogenase) and 14D (compound 21e inhibition of alcohol dehydrogenase).

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A compound comprising:

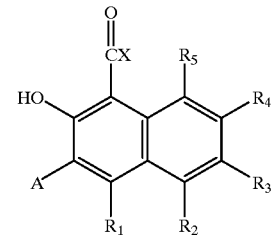

wherein:

A=H or OH;

X=a halogen, OR, NHR, NR'R" where R, R', and R"=H, $C_{1-8}$ alkyl, $C_{2-8}$ alkenyl, or $C_{2-8}$ alkynyl, cycloalkyl, cycloalkenyl aryl or heterocyclic, substituted or unsubstituted;

$R_1$, $R_2$, $R_3$, $R_5$=H, $C_{1-8}$ alkyl, $C_{2-8}$ alkenyl, or $C_{2-8}$ alkynyl, cycloalkyl, cycloalkenyl, aryl, aralkyl or heterocyclic, substituted or unsubstituted, wherein $R_1$ includes at least one methylene spacer through which $R_1$ is attached to said compound; and $R_4$=$C_{1-8}$ alkyl, $C_{2-8}$ alkenyl, or $C_{2-8}$ alkynyl, cycloalkyl, cycloalkenyl, aryl, aralkyl or heterocyclic, substituted or unsubstituted.

2. The compound of claim 1, wherein A=H.
3. The compound of claim 1, wherein A=OH.
4. The compound of claim 1, wherein X=OH.
5. The compound of claim 1, wherein: $R_1$, $R_2$, $R_3$, $R_5$=H or $C_{1-8}$alkyl, $C_{3-8}$cycloalkyl, $C_{2-8}$alkenyl, or $C_{2-8}$ alkynyl, unsubstituted, wherein $R_1$ includes at least one methylene spacer through which $R_1$ is attached to said compound.
6. The compound of claim 1, wherein A=OH, X=OH, $R_1$=$CH_3$, $R_2$=H, $R_3$=$CH_3$, and $R_5$=H.
7. The compound of claim 1, wherein A=OH, X=OH, $R_1$=$CH_3$, $R_2$=H, $R_3$=$CH_3$, $R_4$=$CH_3$, and $R_5$=H.

8. The compound of claim 1, wherein A=OH, X=OH, $R_1$=CH$_2$CH$_2$CH$_3$, $R_2$=H, $R_3$=CH$_3$, $R_4$=CH$_3$, and $R_5$=H.

9. The compound of claim 1, wherein A=OH, X=OH, $R_1$=CH$_2$CH$_2$CH$_3$, $R_2$=H, $R_3$=CH$_3$, $R_4$=CH$_2$C$_6$H$_5$, and $R_5$=H.

10. The compound of claim 1, wherein A=OH, X=OH, $R_1$=CH(CH$_3$)$_2$, $R_2$=H, $R_3$=CH$_3$, $R_4$=CH$_3$, and $R_5$=H.

11. The compound of claim 1, wherein A=OH, X=OH, $R_1$=CH(CH$_3$)$_2$, $R_2$=H, $R_3$=CH$_3$, $R_4$=CH$_2$C$_6$H$_5$, and $R_5$=H.

12. The compound of claim 1, comprising 7-p-trifluoromethylbenzyl-2,3-dihydroxy-6-methyl-4-(1-methylethyl)-1-naphthoicacid.

13. The compound of claim 1, comprising 2,3-dihydroxy-6-methyl-7-(o-methylbenzyl)-4-(1-methylethyl)-1-naphthoicacid.

14. The compound of claim 1, comprising 2,3-dihydroxy-6-methyl-7-(m-methylbenzyl)-4-(1-methylethyl)-1-naphthoicacid.

15. The compound of claim 1, comprising 2,3-dihydroxy-6-methyl-7-(p-methylbenzyl)-4-(1-methylethyl)-1-naphthoicacid.

16. The compound of claim 1, comprising 7-p-chlorobenzyl-2,3-dihydroxy-6-methyl-4-(1-methylethyl)-1-naphthoicacid.

17. A method for making a compound comprising:

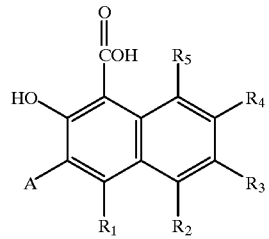

wherein:

A=H or OH; and $R_1$, $R_2$, $R_3$, $R_4$, $R_5$=H, C$_{1-8}$alkyl, C$_{2-8}$alkenyl, or C$_{2-8}$ alkynyl, cycloalkyl, cycloalkenyl, aryl, aralkyl or heterocyclic, substituted or unsubstituted, wherein $R_1$ includes at least one methylene spacer through which $R_1$ is attached to said compound, said method comprising the steps of:

reacting the following compound:

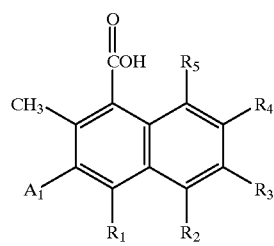

with boron tribromide to form the following compound:

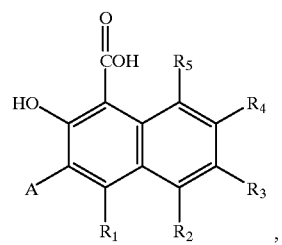

wherein $A_1$ is CH$_3$O or H.

18. The method of claim 17 further comprising the steps of:

reacting the following compound:

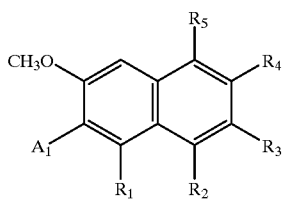

with titanium tetrachloride and dichloromethyl methyl ether to form the following compound:

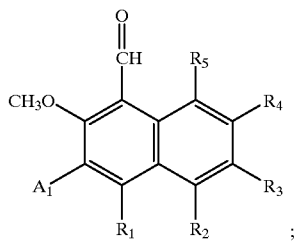

and reacting 1j with sodium hypochlorite to form compound 1k.

19. The method of claim 18 further comprising the steps of:

reacting the following compound

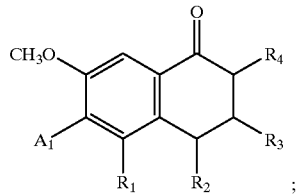

with a Grignard reagent comprising $R_5$MgBr to form compound 1i.

20. The method of claim 18, further comprising the steps of:

reacting the following compound:

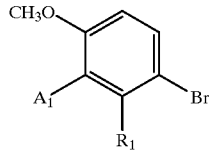

with the following compound:

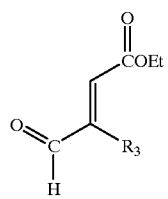

to form the following compound:

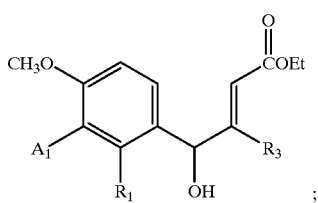

saponifying compound 1c to form the following compound:

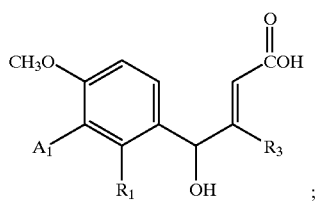

hydrogenolyzing and reducing 1d to form a hydrogenolyzed and reduced carboxylic acid;

cyclizing the hydrogenolyzed and reduced carboxylic acid to form the following compound:

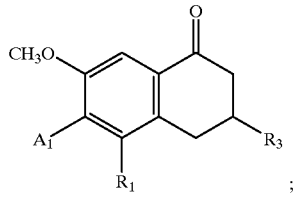

reducing compound 1e to form an intermediate alcohol;

dehydrating the intermediate alcohol to form the following compound:

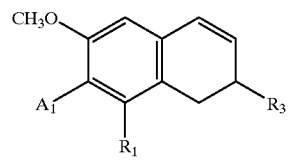

reacting compound 4f with bromine to form a dibromide;
dehydrohalogenating the dibromide to form the following compound:

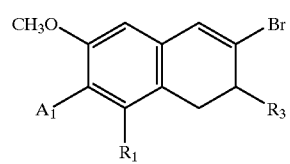

dehydrogenating compound 1g to form the following compound:

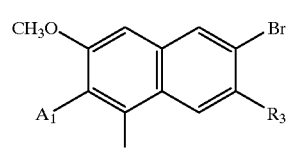

reacting compound 1h with n-butyl lithium and benzaldehyde to form a benzylic alcohol; and
hydrogenolyzing the benzyl alcohol to form compound 1i.

21. The method of claim 20, further comprising the steps of:

reacting the following compound:

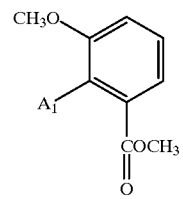

with Grignard reagent to form the following compound:

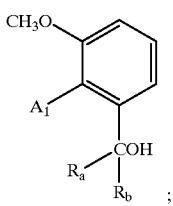

hydrogenolysizing compound 2b to form the following compound:

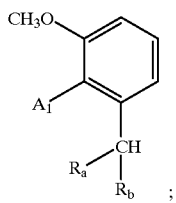

2c and brominating compound 2c to form compound 1a, wherein $R_a$ and $R_b$ are each one of H, $C_{1-8}$ alkyl, $C_{2-8}$ alkenyl, or $C_{2-8}$ alkynyl, cycloalkyl, cycloalkenyl, aryl, aralkyl or heterocyclic, substituted or unsubstituted.

22. The method of claim 20, further comprising the steps of:

reacting the following compound:

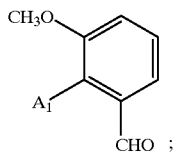

2e with Grignard reagent to form the following compound:

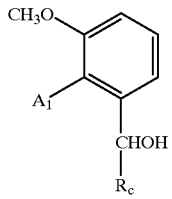

2f hydrogenolyzing compound 2b to form the following compound:

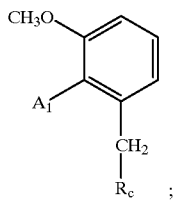

2g and brominating compound 2g to form compound 1a wherein $R_c$ is H, $C_{1-8}$ alkyl, $C_{2-8}$ alkenyl, or $C_{2-8}$ alkynyl, cycloalkyl, cycloalkenyl, aryl, aralkyl or heterocyclic, substituted or unsubstituted.

23. The method of claim 21, further comprising the steps of:

reacting $R_3COCHO$ with methanol to form $R_3COCH(OCH_3)_2$;

reacting $R_3COCH(OCH_3)_2$ with $CH_3CH_2OCOCH_2PO(OEt)_2$ to form $(CH_3O)_2CHCR_3CHCOOEt$; and hydrolyzing $(CH_3O)_2CHCR_3CHCOOEt$ to form compound 1b.

24. The method of claim 18, further comprising the steps of:

reacting the following compound:

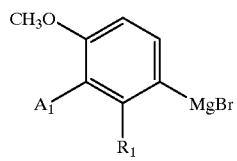

4a with the following compound:

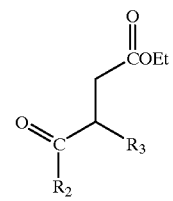

4b to form the following compound:

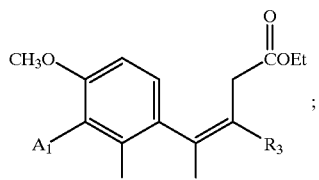

4c saponifying compound 4c to form the following compound:

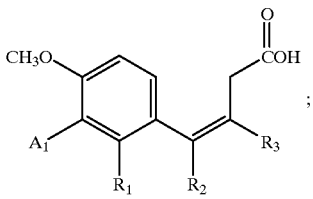

4d hydrogenolyzing and reducing 4d to form a hydrogenolyzed and reduced carboxylic acid;

cyclizing the hydrogenolyzed and reduced carboxylic acid to form the following compound:

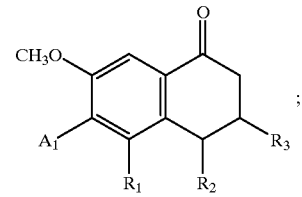

4e reducing compound 4e to form an intermediate alcohol;
dehydrating the intermediate alcohol to form the following compound:

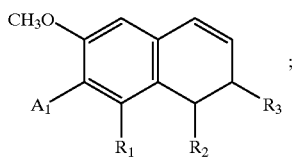

reacting compound 4f with bromine to form a dibromide;
dehydrohalogenating the dibromide to form the following compound:

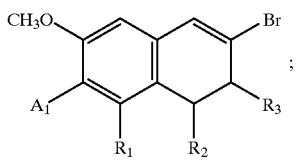

dehydrogenating compound 4g to form the following compound:

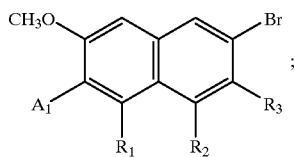

reacting compound 4h with n-butyl lithium and benzaldehyde to form a benzylic alcohol; and hydrogenolyzing the benzyl alcohol to form compound 1i.

25. The method of claim 17, wherein $A_1$ is $CH_3O$ and A is OH.

26. The method of claim 17, wherein $A_1$ and A are each H.

* * * * *